United States Patent

Cho et al.

[11] Patent Number: 5,910,405
[45] Date of Patent: Jun. 8, 1999

[54] HCV DIAGNOSTIC AGENTS

[75] Inventors: Joong Myung Cho; Deog Young Choi; Chun Hyung Kim; Hong Seob So; Jae Young Yang; In Soo Kim; Joo Ho Kim, all of Daejeon, Rep. of Korea

[73] Assignee: Lucky Limited, Seoul, Rep. of Korea

[21] Appl. No.: 08/537,811

[22] PCT Filed: Apr. 29, 1994

[86] PCT No.: PCT/KR94/00040

§ 371 Date: Oct. 24, 1995

§ 102(e) Date: Oct. 24, 1995

[87] PCT Pub. No.: WO94/25486

PCT Pub. Date: Nov. 10, 1994

[30] Foreign Application Priority Data

Apr. 30, 1993 [KR] Rep. of Korea ............... 1993/7440

[51] Int. Cl.$^6$ ............... C12Q 1/70; G01N 33/53; C07K 14/18
[52] U.S. Cl. ............... 435/5; 435/7.1; 435/69.3; 530/300; 530/324; 530/350; 530/811; 530/826
[58] Field of Search ............... 435/5, 7.1, 69.3; 530/300, 324, 350, 811, 826

[56] References Cited

U.S. PATENT DOCUMENTS 5,574,132 11/1996 Lacroix ............... 530/323

FOREIGN PATENT DOCUMENTS 0 521 318   7/1993   European Pat. Off. .
93/17110    9/1993   WIPO ............... C12N 15/51

OTHER PUBLICATIONS

Chang et al., 1991, Mol. Cells 1:507–10.

*Primary Examiner*—Michael P. Woodward
*Assistant Examiner*—Mary K. Zeman
*Attorney, Agent, or Firm*—Pennie & Edmonds, LLP

[57] ABSTRACT

The present invention relates to the epitopes of hepatitis C virus (HCV) core protein and non-structural 3 protein (NS3), and the epitopes of envelope protein, epitopes of non-structural 4 protein, and the epitopes of HCV non-structural 5 protein and a recombinant protein comprising the same; processes for producing the recombinant proteins; an agent for diagnosing antibodies against hepatitis C virus in a putative serum sample, which comprises said recombinant proteins; and a process for diagnosing hepatitis C by using the agent.

7 Claims, 22 Drawing Sheets

```
KHCV COREEPI

.         .        30         .         .        60
ATGAGCACGAATCCTAAACCTCAAAGAAAAACCAAACGTAACACCAACCGCCGCCCACAG
MetSerThrAsnProLysProGlnArgLysThrLysArgAsnThrAsnArgArgProGln

.         .        90         .         .       120
GATATTAAGTTCCCGGGCGGTGGTCAGATCGTTGGTGGAGTTTACTTGTTGCCGCGCAGG
AspIleLysPheProGlyGlyGlyGlnIleValGlyGlyValTyrLeuLeuProArgArg

.         .       150         .         .       180
GGCCCCAGGTTGGGTGTGCGCGCGACTAGGAAGACTTCCGAGCGGTCGCAACCTCGTGGA
GlyProArgLeuGlyValArgAlaThrArgLysThrSerGluArgSerGlnProArgGly

.         .       210         .         .       240
AGGCGACAGCCTATCCCCAAGGCTCGCCGGCCCGAGGGCAGGGCCTGGGCTCAGCCCGGG
ArgArgGlnProIleProLysAlaArgArgProGluGlyArgAlaTrpAlaGlnProGly

.         .       270         .         .       300
TACCCTTGGCCCCTCTATGGCAATGAGGGCTTGGGGTGGGCAGGATGGCTCCTGTCACCC
TyrProTrpProLeuTyrGlyAsnGluGlyLeUGlyTrpAlaGlyTrpLeuLeuSerPro

CGCGGC
ArgGly
```

FIG.1A

KHCV 518

1   ATCACCAGGTGCCCTATCACATACTCCACCTATGGCAAGTTCCTTGCCGACGGTGGC
    IleThrThrGlyAlaProIleThrTyrSerThrTyrGlyLysPheLeuAlaAspGlyGly

61  GGCTCCGGGGGCGCCTATGACATCATAATGTGTGATGAGTGCCACTCAACTGACTGACT
    GlySerGlyGlyAlaTyrAspIleIleMetCysAspGluCysHisSerThrAspSerThr

121 ACCATTTATGGCATGGACACAGTCCTGGACCAAGCGGAGACGGCTGGAGCGCGGCTCGTG
    ThrIleTyrGlyIleGlyThrValLeuAspGlnAlaGluThrAlaGlyAlaArgLeuVal

181 GTGCTCTCCACCGCTAGCCCTCCGGGATCGGTCACCGTGCCACACCTCAATATCGAGGAG
    ValLeuSerThrAlaThrProProGlySerValThrValProHisLeuAsnIleGluGlu

241 GTGGCCCTGTCTAATACTGGAGAGATCCCCTTCTACGGCAAAGCCATTCCCATCGAGGCT
    ValAlaLeuSerAsnThrGlyGluIleProPheTyrGlyLysAlaIleProIleGluAla

301 ATCAAGGGGGAAGGCATCTCATTTCTGCCATTCCAAGAAGAAGTGTGACGAACTCGCC
    IleLysGlyGlyArgHisLeuIlePheCysHisSerLysLysLysCysAspGluLeuAla

361 GCAAAGCTGTCAGGCCTCGGACTCAATGCCGTAGCGGTATTACCGGGGTCTTGACGTGTCC
    AlaLysLeuSerGlyLeuGlyLeuAsnAlaValAlaValAlaTyrArgGlyLeuAspValSer

421 GTCATACCGACCAGGGAGACGTTGTTGTCGGGCAGGACGACGCTCTAATGACGGGCTTT
    ValIleProThrSerGlyAspValValValAlaThrAspAlaLeuMetThrGlyPhe

481 ACCGGGGACTTTGACTCAGTGATCGACTGTAATACGTGT
    ThrGlyAspPheAspSerValIleAspCysAsnThrCys

FIG. 1B

```
    KHCV NS4E

1 ATCATCCCCGATAGGGAAGTTCTCTACCAGGAGTTCGACGAGATGGAGGAGTGTGCCTCA
    IleIleProAspArgGluValLeuTyrGlnGluPheAspGluMetGluGluCysAlaSer

61 CACCTCCCTTACTTCGAACAGGGAATGCAGCTCGCCGAGCAATTCAAACAGAAGGCGCTC
    HisLeuProTyrPheGluGlnGlyMetGlnLeuAlaGluGlnPheLysGlnLysAlaLeu

121 GGGTTG
    GlyLeu

KHCV E1G

1 GTTTCCCAGCTGTTCACCTTTTCGCCTCGCCGGCATGAGACGGTACAGGACTGCAACTGC
    ValSerGlnLeuPheThrPheSerProArgArgHisGluThrValGlnAspCysAsnCys

61 TCAATCTATCCCGGCCGCGTATCAGGTCACCGCATGGCCTGGGATATGATGATGAACTGG
    SerIleTyrProGlyArgValSerGlyHisArgMetAlaTrpAspMetMetMetAsnTrp

121 TCGCCTACAACAGCCCTAGTGGTATCGCAGCTACTCCGGATCCCACAAGCTGTCGTGGAC
    SerProThrThrAlaLeuValValSerGlnLeuLeuArgIleProGlnAlaValValAsp

181 ATGGTGACAGGGTCCCACTGGGGAATCCTGGCGGGCCTTGCCTACTATTCCATGGTGGGG
    MetValThrGlySerHisTrpGlyIleLeuAlaGlyLeuAlaTyrTyrSerMetValGly

241 AACTGGGCTAAGGTCTTAATTGCGATGCTACTCTTTGCCGGCGTTGACGGAACCACCCAC
    AsnTrpAlaLysValLeuIleAlaMetLeuLeuPheAlaGlyValAspGlyThrThrHis

301 GTGACAGGG
    ValThrGly
```

FIG.2A

KHCV E2A

```
  1  GGGGCGCAAGGTCGGGCCGCTAGCTCGCTAACGTCCCTCTTTAGCCCTGGGCCGGTTCAG
     GlyAlaGlnGlyArgAlaAlaSerSerLeuThrSerLeuPheSerProGlyProValGln

61  CACCTCCAGCTCATAAACACCAACGGCAGCTGGATATCAACAGGACCGCCCTGAGCTGC
     HisLeuGlnLeuIleAsnThrAsnGlySerTrpHisIleAsnArgThrAlaLeuSerCys

121  AATGACTCCCTCAACACTGGGTTTGTTGCCGCGCTGTTCTACAAATACAGGTTCAACGCG
     AsnAspSerLeuAsnThrGlyPheValAlaAlaLeuPheTyrLysTyrArgPheAsnAla

181  TCCGGGGTGCCCGGAGCGCTTGGCCAGTGCCGCCCCATTGATACATTCGGCGCAGGGTGG
     SerGlyCysProGluArgLeuAlaThrCysArgProIleAspThrPheAlaGlnGlyTrp
```

KHCV E2E

```
  1  ACTCGGGGAGAGCGTTGTGACCTGGAGGACAGGATAGGTCAGAGCTTAGCCCGCTGCTG
     ThrArgGlyGluArgCysAspLeuGluAspArgAspArgSerGluLeuSerProLeuLeu

61  CTGTCTACAACAGAGTGCAGGTACTGCCCTGTTCCTTCACAACCCTACCGGCTCTGTCC
     LeuSerThrThrGluTrpGlnValLeuProCysSerPheThrThrLeuProAlaLeuSer

121  ACTGGTTTGATTCATTCCATCAGAACATCGTGGACATACAATACCTGTACGGTATAGGG
     ThrGlyLeuIleHisSerIleGlnAsnIleValAspIleGlnTyrLeuTyrGlyIleGly

181  TCGGCGGGTTGTCTCCTTTGCGATCAAATGGGAGTATATTGTGCTGCTCTTCCTTCTCTG
     SerAlaValValSerPheAlaIleLysTrpGluTyrIleValLeuLeuPheLeuLeuLeu

241  GCGGACGCG
     AlaAspAla
```

FIG. 2B

KHCV NS5-1.2

```
  1 ACGGGCATGACCACTGACAACGTGAAGTGTCCATGCCAGGTTCCGGCCCCCGAATTCTTC
    ThrGlyMetThrThrAspAsnValLysCysProCysGlnValProAlaProGluPhePhe

61 ACGGAGGTGGATGGAGTGCGGTTGCACAGGTACGCTCCGGCGTGCAGACCTCTCCTACGG
    ThrGluValAspGlyValArgLeuHisArgTyrAlaProAlaCysArgProLeuLeuArg

121 GAGGAGGTCGTATTCCAGGTCGGGCTCCACCAGTACCTGGTCGGGTCACAGCTCCCATGC
    GluGluValValPheGlnValGlyLeuHisGlnTyrLeuValGlySerGlnLeuProCys

181 GAGCCCGAACCGGATGTAGCAGTGCTCACTTCCATGCTCACTGACCCCTCCCACATTACA
    GluProGluProAspValAlaValLeuThrSerMetLeuThrAspProSerHisIleThr

241 GCAGAGACGGCTAAGCGTAGGCTGGCCAGGGGGTCTCCCCCCTCCTTGGCCAGCTCTTCA
    AlaGluThrAlaLysArgArgLeuAlaArgGlySerProProSerLeuAlaSerSerSer

301 GCTAGCCAGTTGTCTGCGCCTTCCTTGAAGGCGACATGCACTACCCATCATGACTCCCCG
    AlaSerGlnLeuSerAlaProSerLeuLysAlaThrCysThrThrHisHisAspSerPro

361 GACGCTGACCTCATTGAGGCCAACCTCTTGTGGCGGCAAGAGATGGGCGGGAACATCACC
    AspAlaAspLeuIleGluAlaAsnLeuLeuTrpArgGlnGluMetGlyGlyAsnIleThr

421 CGCGTGGAGTCAGAGAATAAGGTGGTAATCCTGGACTCTTTCGACCCGCTCCGAGCGGAG
    ArgValGluSerGluAsnLysValValIleLeuAspSerPheAspProLeuArgAlaGlu

481 GATGATGAGGGGGAAATATCCGTTCCGGCGGAGATCCTGCGGAAATCCAGGAAATTCCCC
    AspAspGluGlyGluIleSerValProAlaGluIleLeuArgLysSerArgLysPhePro

541 CCAGCGCTGCCCATATGGGCGCCGCCGGATTACAACCCTCCGCTGCTAGAGTCCTGGAAG

ProAlaLeuProIleTrpAlaProProAspTyrAsnProProLeuLeuGluSerTrpLys
```

FIG.3A

601  GACCCGGACTACGTTCCTCCGGTGGTACACGGGTGCCGTTGCCGCCCACCAAGGCCCT
     AspProAspTyrValProProValValHisGlyCysProLeuProProThrLysAlaPro

661  CCAATACCACCTCCACGGAGGAAGAGACGGTTGTCCTGACAGAATCCACGTGTCTTCT
     ProIleProProProArgLysArgThrValValLeuThrGluSerThrValSerSer

721  GCCTTGGCGGAGCTCGCTACTAAGACCTTCGGCCAGCTCGGATGTCGGCCATGACAGC
     AlaLeuAlaGluLeuAlaThrLysThrPheGlySerSerGlySerAlaIleAspSer

781  GGTACGGGCACCGCCCCTCCTGACCAAGCTCCGGTGACGGCGACAGAGAGTCCGACGTT
     GlyThrAlaThrAlaProProAspGlnAlaSerGlyAspGlyAspArgGluSerAspVal

841  GAGTCGTTCTCCTCCATGCCCCCCCTTGAGGGAGAGCCGGGGGACCCCGATCTCAGCGAC
     GluSerPheSerSerMetProProLeuGluGluGluProGlyAspProLeuSerAsp

901  GGATCTTGGTCCACCGTGAGCGAGGAGGCTAGTGAGGACGTCGTCTGCTGTTCGATGTCC
     GlySerTrpSerThrValSerGluGluAlaSerGluAspValValCysCysSerMetSer

961  TACACATGGACAGGACGCCCTGATCACGCCCATGCGCTGCCGAGGAAAGCAAGTTGCCCATC
     TyrThrTrpThrGlyAlaLeuIleThrProCysAlaAlaGluGluSerLysLeuProIle

1021 AACCCGTTGAGCAATTCTTTGCTACGTCACCACAACATGGTCTATGCTACAACATCCCGC
     AsnProLeuSerAsnSerLeuLeuArgHisHisAsnMetValTyrAlaThrThrSerArg

1081 AGCGCAGGCCTGCGGCAGAAGAAGGTCACCTTTGACAGACTGCAAGTCCTGGACGACCAC
     SerAlaGlyLeuArgGlnLysLysValThrPheAspArgLeuGlnValLeuAspAspHis

1141 TACCGGGACGTGCTTAAGGAGATGAAGGCGAAGGCG
     TyrArgAspValLeuLysGluMetLysAlaLysAla

FIG.3B

NdeI  SacII  SalI

| UBIQUITIN | KHCV ENVELOPE cDNA SEGMENT |

TRPp ptrpH-UB-SEGMENT

PstI

ORI

FIG.8

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer P897T2

(xi) SEQUENCE DESCRIPTION: SEQ ID NO:1:

TGAGACTCCG CGGTGGTGCG GTGGAATTCA TACCCGTT     38

(2) INFORMATION FOR SEQ ID NO:2:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer P518T2

(xi) SEQUENCE DESCRIPTION: SEQ ID NO:2:

TGAGACTCCG CGGTGGTATC ACCACAGGCG CCCCTATC     38

(2) INFORMATION FOR SEQ ID NO:3:

(i) SEQUENCE CHARACTERISTICS:

```
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer P365T2

(xi) SEQUENCE DESCRIPTION: SEQ ID NO:3:

TGAGACTCCG CGGTGGTGCG GAGACGGCTG GAGCGCGG                          38

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer P257T2

(xi) SEQUENCE DESCRIPTION: SEQ ID NO:4:

TGAGACTCCG CGGTGGTAAC ATTGGAGAGA TTCCTTTC                          38

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer P150T2

(xi) SEQUENCE DESCRIPTION: SEQ ID NO:5:

TGAGACTCCG CGGTGGTTTG TCCCTCGGAG TCAATGCT                          38

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer P897SAL (xi) SEQUENCE DESCRIPTION: SEQ ID NO:6:

GACTGGACTA TTAACACGTA TTACAGTCGA TCAC                              34

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (ix) FEATURE:
```

(D) OTHER INFORMATION: primer P652SAL (xi) SEQUENCE DESCRIPTION: SEQ ID NO:7:

GACTGGACTA TTACAGCTTT GCAGCGAGCT CGTC                              34

(2) INFORMATION FOR SEQ ID NO:8:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: Other (ix) FEATURE:
            (D) OTHER INFORMATION: primer P570SAL (xi) SEQUENCE DESCRIPTION: SEQ ID NO:8:

GACTGGACTA TTAGAGGGGG ATGGCTTTGC CATA                              34

(2) INFORMATION FOR SEQ ID NO:9:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: Other (ix) FEATURE:
            (D) OTHER INFORMATION: primer P430SAL (xi) SEQUENCE DESCRIPTION: SEQ ID NO:9:

GACTGGACTA TTATTGGTCC AGGACCGTGC CAAT                              34

(2) INFORMATION FOR SEQ ID NO:10:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: Other (ix) FEATURE:
            (D) OTHER INFORMATION: primer P290SAL (xi) SEQUENCE DESCRIPTION: SEQ ID NO:10:

GACTGGACTA TTAGGCGCCT GTGGTGATGG TCCT                              34

(2) INFORMATION FOR SEQ ID NO:11:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: Other (ix) FEATURE:
            (D) OTHER INFORMATION: primer PE1T2

(xi) SEQUENCE DESCRIPTION: SEQ ID NO:11:

TGAGACTCCG CGGTGGTTAT GAAGTGGGCA ACGCGTCC                          38

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE1DT2

(xi) SEQUENCE DESCRIPTION: SEQ ID NO:12:

TGAGACTCCG CGGTGGTGAC TTGCTCGTTG GGGTAGCT                                    38

(2) INFORMATION FOR SEQ ID NO:13:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE1EGT2

(xi) SEQUENCE DESCRIPTION: SEQ ID NO:13:

TGAGACTCCG CGGTGGTGTT TCCCAGCTGT TCACCTTC                                    38

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE1FT2

(xi) SEQUENCE DESCRIPTION: SEQ ID NO:14:

TGAGACTCCG CGGTGGTACA ACAGCCCTAG TGGTATCG                                    38

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE1AXHO (xi) SEQUENCE DESCRIPTION: SEQ ID NO:15:

AAAAAACTCG AGTTAGACAT GGCGTCGCAA TGTCGT                                      36

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other

```
        (ix) FEATURE:
             (D) OTHER INFORMATION: primer PE1BXHO (xi) SEQUENCE DESCRIPTION: SEQ ID NO:16:

AAAAAACTCG AGTTAAAGGA AAACAGATCC GCAGAG                                    36

(2) INFORMATION FOR SEQ ID NO:17:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: Other (ix) FEATURE:
             (D) OTHER INFORMATION: primer PE1CDEXHO (xi) SEQUENCE DESCRIPTION: SEQ ID NO:17:

AAAAAACTCG AGTTAAGGCG ACCAGTTCAT CATCAT                                    36

(2) INFORMATION FOR SEQ ID NO:18:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: Other (ix) FEATURE:
             (D) OTHER INFORMATION: primer PE1XHO (xi) SEQUENCE DESCRIPTION: SEQ ID NO:18:

AAAAAACTCG AGTTACCCTG TCACGTGGGT GGTTCC                                    36

(2) INFORMATION FOR SEQ ID NO:19:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: Other (ix) FEATURE:
             (D) OTHER INFORMATION: primer PE2T2

(xi) SEQUENCE DESCRIPTION: SEQ ID NO:19:

TGAGACTCCG CGGTGGTGGG GCGCAAGGTC GGGCCGCT                                  38

(2) INFORMATION FOR SEQ ID NO:20:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (ii) MOLECULE TYPE: Other (ix) FEATURE:
             (D) OTHER INFORMATION: primer PE2BT2

(xi) SEQUENCE DESCRIPTION: SEQ ID NO:20:

TGAGACTCCG CGGTGGTGGT CCCATCACTT ACACTGAG                                  38
```

(2) INFORMATION FOR SEQ ID NO:21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE2DFT2

(xi) SEQUENCE DESCRIPTION: SEQ ID NO:21:

```
TGAGACTCCG CGGTGGTGGC ACTGGGTTCA CCAAGACA                                 38
```

(2) INFORMATION FOR SEQ ID NO:22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE2ET2

(xi) SEQUENCE DESCRIPTION: SEQ ID NO:22:

```
TGAGACTCCG CGGTGGTACT CGGGGAGAGC GTTGTGAC                                 38
```

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE2AXHO (xi) SEQUENCE DESCRIPTION: SEQ ID NO:23:

```
AAAAAACTCG AGTTACCACC CCTGCGCGAA TGTATC                                   36
```

(2) INFORMATION FOR SEQ ID NO:24:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE2BCXHO (xi) SEQUENCE DESCRIPTION: SEQ ID NO:24:

```
AAAAAACTCG AGTTAATTCA TCCAGGTACA ACCGAA                                   36
```

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (ix) FEATURE:
    (D) OTHER INFORMATION: primer PE2DXHO (xi) SEQUENCE DESCRIPTION: SEQ ID NO:25:

AAAAAACTCG AGTTACCAGT TGCATGCGGC GTCGAG                                    36

(2) INFORMATION FOR SEQ ID NO:26:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE2XHO (xi) SEQUENCE DESCRIPTION: SEQ ID NO:26:

AAAAAACTCG AGTTACGCGT CCGCCAGAAG AAGGAAGAG                                 39

(2) INFORMATION FOR SEQ ID NO:27:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PK518T2

(xi) SEQUENCE DESCRIPTION: SEQ ID NO:27:

TGAGACTCCG CGGTGGTGGA GGAGGAGGAG GAGGAATCAC CACAGGCGCC CCTATC              56

(2) INFORMATION FOR SEQ ID NO:28:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PK518SAL (xi) SEQUENCE DESCRIPTION: SEQ ID NO:28:

AAAAAAGTCG ACTATTAACA CGTATTACAG TCGATCAC                                  38

(2) INFORMATION FOR SEQ ID NO:29:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PNS4ET2

(xi) SEQUENCE DESCRIPTION: SEQ ID NO:29:

```
TGAGACTCCG CGGTGGTATC ATCCCCGATA GGGAAGTT                                38
```

(2) INFORMATION FOR SEQ ID NO:30:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PNS4ESAL (xi) SEQUENCE DESCRIPTION: SEQ ID NO:30:

```
AAAAAAGTCG ACTATTACAA CCCGAGCGCC TTCTGTTT                                38
```

(2) INFORMATION FOR SEQ ID NO:31:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PE2EGE1G (xi) SEQUENCE DESCRIPTION: SEQ ID NO:31:

```
TTCCTTCTTC TGGCGGACGC GGTTTCCCAG CTGTTCACCT TC                           42
```

(2) INFORMATION FOR SEQ ID NO:32:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PNS4EGE2C3

(xi) SEQUENCE DESCRIPTION: SEQ ID NO:32:

```
CAGAAGGCGC TCGGGTTGCC AGGAGGAGGA GGTGGTACTC GGGGAGAGCG TTGT             54
```

(2) INFORMATION FOR SEQ ID NO:33:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (ix) FEATURE:
        (D) OTHER INFORMATION: primer PNS5T2

(xi) SEQUENCE DESCRIPTION: SEQ ID NO:33:

```
TGAGACTCCG CGGTGGTACG GGCATGACCA CTGACAAC                                38
```

(2) INFORMATION FOR SEQ ID NO:34:

(i) SEQUENCE CHARACTERISTICS:
        (A) LENGTH: 38 base pairs
        (B) TYPE: nucleic acid (C) STRANDEDNESS: single
(D) TOPOLOGY: linear (ii) MOLECULE TYPE: Other (ix) FEATURE:
    (D) OTHER INFORMATION: primer PNS5-1.2SAL (xi) SEQUENCE DESCRIPTION: SEQ ID NO:34:

```
AAAAAAGTCG ACTATTACGC CTTCCCCTTC ATCTCCTT                             38
```

(2) INFORMATION FOR SEQ ID NO:35:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: cDNA (ix) FEATURE:
        (D) OTHER INFORMATION: KHCV COREEPI, Fig. 1

(xi) SEQUENCE DESCRIPTION: SEQ ID NO:35:

```
ATGAGCACGA ATCCTAAACC TCAAAGAAAA ACCAAACGTA ACACCAACCG CCGCCCACAG     60

GATATTAAGT TCCCGGGCGG TGGTCAGATC GTTGGTGGAG TTTACTTGTT GCCGCGCAGG    120

GGCCCCAGGT TGGGTGTGCG CGCGACTAGG AAGACTTCCG AGCGGTCGCA ACCTCGTGGA    180

AGGCGACAGC CTATCCCCAA GGCTCGCCGG CCCGAGGGCA GGGCCTGGGC TCAGCCCGGG    240

TACCCTTGGC CCCTCTATGG CAATGAGGGC TTGGGGTGGG CAGGATGGCT CCTGTCACCC    300

CGCGGC                                                               306
```

(2) INFORMATION FOR SEQ ID NO:36:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (ii) MOLECULE TYPE: cDNA (ix) FEATURE:
        (D) OTHER INFORMATION: KHCV 518, Fig. 1

(xi) SEQUENCE DESCRIPTION: SEQ ID NO:36:

```
ATCACCACAG GTGCCCCTAT CACATACTCC ACCTATGGCA AGTTCCTTGC CGACGGTGGC     60

GGCTCCGGGG GCGCCTATGA CATCATAATG TGTGATGAGT GCCACTCAAC TGACTCGACT    120

ACCATTTATG GCATCGGCAC AGTCCTGGAC CAAGCGGAGA CGGCTGGAGC GCGGCTCGTG    180

GTGCTCTCCA CCGCTACGCC TCCGGGATCG GTCACCGTGC CACACCTCAA TATCGAGGAG    240

GTGGCCCTGT CTAATACTGG AGAGATCCCC TTCTACGGCA AAGCCATTCC CATCGAGGCT    300

ATCAAGGGGG GAAGGCATCT CATTTTCTGC CATTCCAAGA AGAAGTGTGA CGAACTCGCC    360

GCAAAGCTGT CAGGCCTCGG ACTCAATGCC GTAGCGTATT ACCGGGGTCT TGACGTGTCC    420

GTCATACCGA CCAGCGGAGA CGTTGTTGTC GTGGCGACGG ACGCTCTAAT GACGGGCTTT    480

ACCGGCGACT TTGACTCAGT GATCGACTGT AATACGTGT                           519
```

(2) INFORMATION FOR SEQ ID NO:37:

(i) SEQUENCE CHARACTERISTICS:
        (A) LENGTH: 126 base pairs
        (B) TYPE: nucleic acid (C) STRANDEDNESS: single
           (D) TOPOLOGY: linear (ii) MOLECULE TYPE: cDNA (ix) FEATURE:
           (D) OTHER INFORMATION: KHCV NS4E, Fig. 2

(xi) SEQUENCE DESCRIPTION: SEQ ID NO:37:

ATCATCCCCG ATAGGGAAGT TCTCTACCAG GAGTTCGACG AGATGGAGGA GTGTGCCTCA    60

CACCTCCCTT ACTTCGAACA GGGAATGCAG CTCGCCGAGC AATTCAAACA GAAGGCGCTC   120

GGGTTG                                                             126

(2) INFORMATION FOR SEQ ID NO:38:

(i) SEQUENCE CHARACTERISTICS:
           (A) LENGTH: 309 base pairs
           (B) TYPE: nucleic acid
           (C) STRANDEDNESS: single
           (D) TOPOLOGY: linear (ii) MOLECULE TYPE: cDNA (ix) FEATURE:
           (D) OTHER INFORMATION: KHCV E1G, Fig. 2

(xi) SEQUENCE DESCRIPTION: SEQ ID NO:38:

GTTTCCCAGC TGTTCACCTT TTCGCCTCGC CGGCATGAGA CGGTACAGGA CTGCAACTGC    60

TCAATCTATC CCGGCCGCGT ATCAGGTCAC CGCATGGCCT GGGATATGAT GATGAACTGG   120

TCGCCTACAA CAGCCCTAGT GGTATCGCAG CTACTCCGGA TCCCACAAGC TGTCGTGGAC   180

ATGGTGACAG GTCCCACTG GGGAATCCTG GCGGGCCTTG CCTACTATTC CATGGTGGGG    240

AACTGGGCTA AGGTCTTAAT TGCGATGCTA CTCTTTGCCG GCGTTGACGG AACCACCCAC   300

GTGACAGGG                                                          309

(2) INFORMATION FOR SEQ ID NO:39:

(i) SEQUENCE CHARACTERISTICS:
           (A) LENGTH: 240 base pairs
           (B) TYPE: nucleic acid
           (C) STRANDEDNESS: single
           (D) TOPOLOGY: linear (ii) MOLECULE TYPE: cDNA (ix) FEATURE:
           (D) OTHER INFORMATION: KHCV E2A, Fig. 2

(xi) SEQUENCE DESCRIPTION: SEQ ID NO:39:

GGGGCGCAAG GTCGGGCCGC TAGCTCGCTA ACGTCCCTCT TTAGCCCTGG GCCGGTTCAG    60

CACCTCCAGC TCATAAACAC CAACGGCAGC TGGCATATCA ACAGGACCGC CCTGAGCTGC   120

AATGACTCCC TCAACACTGG GTTTGTTGCC GCGCTGTTCT ACAAATACAG GTTCAACGCG   180

TCCGGGTGCC CGGAGCGCTT GGCCACGTGC CGCCCCATTG ATACATTCGC GCAGGGGTGG   240

(2) INFORMATION FOR SEQ ID NO:40:

(i) SEQUENCE CHARACTERISTICS:
           (A) LENGTH: 249 base pairs
           (B) TYPE: nucleic acid
           (C) STRANDEDNESS: single
           (D) TOPOLOGY: linear (ii) MOLECULE TYPE: cDNA (ix) FEATURE:

(D) OTHER INFORMATION: KHCV E2E, Fig. 2

(xi) SEQUENCE DESCRIPTION: SEQ ID NO:40:

ACTCGGGGAG AGCGTTGTGA CCTGGAGGAC AGGGATAGGT CAGAGCTTAG CCCGCTGCTG    60

CTGTCTACAA CAGAGTGGCA GGTACTGCCC TGTTCCTTCA CAACCCTACC GGCTCTGTCC   120

ACTGGTTTGA TTCATCTCCA TCAGAACATC GTGGACATAC AATACCTGTA CGGTATAGGG   180

TCGGCGGTTG TCTCCTTTGC GATCAAATGG GAGTATATTG TGCTGCTCTT CCTTCTTCTG   240

GCGGACGCG                                                          249

(2) INFORMATION FOR SEQ ID NO:41:

(i) SEQUENCE CHARACTERISTICS:
        (A) LENGTH: 1176 base pairs
        (B) TYPE: nucleic acid
        (C) STRANDEDNESS: single
        (D) TOPOLOGY: linear (ii) MOLECULE TYPE: cDNA (ix) FEATURE:
        (D) OTHER INFORMATION: KHCV NS5-1.2, Fig. 3

(xi) SEQUENCE DESCRIPTION: SEQ ID NO:41:

ACGGGCATGA CCACTGACAA CGTGAAGTGT CCATGCCAGG TTCCGGCCCC CGAATTCTTC    60

ACGGAGGTGG ATGGAGTGCG GTTGCACAGG TACGCTCCGG CGTGCAGACC TCTCCTACGG   120

GAGGAGGTCG TATTCCAGGT CGGGCTCCAC CAGTACCTGG TCGGGTCACA GCTCCCATGC   180

GAGCCCGAAC CGGATGTAGC AGTGCTCACT TCCATGCTCA CTGACCCCTC CCACATTACA   240

GCAGAGACGG CTAAGCGTAG GCTGGCCAGG GGGTCTCCCC CCTCCTTGGC CAGCTCTTCA   300

GCTAGCCAGT TGTCTGCGCC TTCCTTGAAG GCGACATGCA CTACCCATCA TGACTCCCCG   360

GACGCTGACC TCATTGAGGC CAACCTCTTG TGGCGGCAAG AGATGGGCGG GAACATCACC   420

CGCGTGGAGT CAGAGAATAA GGTGGTAATC CTGGACTCTT TCGACCCGCT CCGAGCGGAG   480

GATGATGAGG GGGAAATATC CGTTCCGGCG GAGATCCTGC GGAAATCCAG GAAATTCCCC   540

CCAGCGCTGC CCATATGGGC GCCGCCGGAT TACAACCCTC CGCTGCTAGA GTCCTGGAAG   600

GACCCGGACT ACGTTCCTCC GGTGGTACAC GGGTGCCCGT TGCCGCCCAC CAAGGCCCCT   660

CCAATACCAC CTCCACGGAG GAAGAGGACG GTTGTCCTGA CAGAATCCAC CGTGTCTTCT   720

GCCTTGGCGG AGCTCGCTAC TAAGACCTTC GGCAGCTCCG GATCGTCGGC CATCGACAGC   780

GGTACGGCGA CCGCCCCTCC TGACCAAGCC TCCGGTGACG GCGACAGAGA GTCCGACGTT   840

GAGTCGTTCT CCTCCATGCC CCCCCTTGAG GGAGAGCCGG GGACCCCGA TCTCAGCGAC   900

GGATCTTGGT CCACCGTGAG CGAGGAGGCT AGTGAGGACG TCGTCTGCTG TTCGATGTCC   960

TACACATGGA CAGGCGCCCT GATCACGCCA TGCGCTGCGG AGGAAAGCAA GTTGCCCATC  1020

AACCCGTTGA GCAATTCTTT GCTACGTCAC CACAACATGG TCTATGCTAC AACATCCCGC  1080

AGCGCAGGCC TGCGGCAGAA GAAGGTCACC TTTGACAGAC TGCAAGTCCT GGACGACCAC  1140

TACCGGGACG TGCTTAAGGA GATGAAGGCG AAGGCG                            1176

(2) INFORMATION FOR SEQ ID NO:42:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
    (D) OTHER INFORMATION: KHCV COREEPI, Fig.1

(xi) SEQUENCE DESCRIPTION: SEQ ID NO:42:

Met Ser Thr Asn Pro Lys Pro Gln Arg Lys Thr Lys Arg Asn Thr Asn
1               5                   10                  15

Arg Arg Pro Gln Asp Ile Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
50                          55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly
                100

(2) INFORMATION FOR SEQ ID NO:43:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: protein (ix) FEATURE:
        (D) OTHER INFORMATION: KHCV 518, Fig. 1

(xi) SEQUENCE DESCRIPTION: SEQ ID NO:43:

Ile Thr Thr Gly Ala Pro Ile Thr Tyr Ser Thr Tyr Gly Lys Phe Leu
1               5                   10                  15

Ala Asp Gly Gly Gly Ser Gly Gly Ala Tyr Asp Ile Ile Met Cys Asp
            20                  25                  30

Glu Cys His Ser Thr Asp Ser Thr Thr Ile Tyr Gly Ile Gly Thr Val
            35                  40                  45

Leu Asp Gln Ala Glu Thr Ala Gly Ala Arg Leu Val Val Leu Ser Thr
50                          55                  60

Ala Thr Pro Pro Gly Ser Val Thr Val Pro His Leu Asn Ile Glu Glu
65                  70                  75                  80

Val Ala Leu Ser Asn Thr Gly Glu Ile Pro Phe Tyr Gly Lys Ala Ile
                85                  90                  95

Pro Ile Glu Ala Ile Lys Gly Gly Arg His Leu Ile Phe Cys His Ser
            100                 105                 110

Lys Lys Lys Cys Asp Glu Leu Ala Ala Lys Leu Ser Gly Leu Gly Leu
            115                 120                 125

Asn Ala Val Ala Tyr Tyr Arg Gly Leu Asp Val Ser Val Ile Pro Thr
130                         135                 140

Ser Gly Asp Val Val Val Val Ala Thr Asp Ala Leu Met Thr Gly Phe
145                 150                 155                 160

Thr Gly Asp Phe Asp Ser Val Ile Asp Cys Asn Thr Cys
                165                 170

(2) INFORMATION FOR SEQ ID NO:44:

(i) SEQUENCE CHARACTERISTICS:

-continued (A) LENGTH: 42 amino acids
(B) TYPE: amino acid
(C) STRANDEDNESS: single
(D) TOPOLOGY: linear (ii) MOLECULE TYPE: protein (ix) FEATURE:
(D) OTHER INFORMATION: KHCV NS4E, Fig. 2

(xi) SEQUENCE DESCRIPTION: SEQ ID NO:44:

```
Ile Ile Pro Asp Arg Glu Val Leu Tyr Gln Glu Phe Asp Glu Met Glu
 1               5                  10                  15

Glu Cys Ala Ser His Leu Pro Tyr Phe Glu Gln Gly Met Gln Leu Ala
            20                  25                  30

Glu Gln Phe Lys Gln Lys Ala Leu Gly Leu
        35                  40
```

(2) INFORMATION FOR SEQ ID NO:45:

(i) SEQUENCE CHARACTERISTICS:
(A) LENGTH: 103 amino acids
(B) TYPE: amino acid
(C) STRANDEDNESS: single
(D) TOPOLOGY: linear (ii) MOLECULE TYPE: protein (ix) FEATURE:
(D) OTHER INFORMATION: KHCV E1G, Fig. 2

(xi) SEQUENCE DESCRIPTION: SEQ ID NO:45:

```
Val Ser Gln Leu Phe Thr Phe Ser Pro Arg Arg His Glu Thr Val Gln
 1               5                  10                  15

Asp Cys Asn Cys Ser Ile Tyr Pro Gly Arg Val Ser Gly His Arg Met
            20                  25                  30

Ala Trp Asp Met Met Met Asn Trp Ser Pro Thr Thr Ala Leu Val Val
        35                  40                  45

Ser Gln Leu Leu Arg Ile Pro Gln Ala Val Val Asp Met Val Thr Gly
    50                  55                  60

Ser His Trp Gly Ile Leu Ala Gly Leu Ala Tyr Tyr Ser Met Val Gly
65                  70                  75                  80

Asn Trp Ala Lys Val Leu Ile Ala Met Leu Leu Phe Ala Gly Val Asp
                85                  90                  95

Gly Thr Thr His Val Thr Gly
            100
```

(2) INFORMATION FOR SEQ ID NO:46:

(i) SEQUENCE CHARACTERISTICS:
(A) LENGTH: 80 amino acids
(B) TYPE: amino acid
(C) STRANDEDNESS: single
(D) TOPOLOGY: linear (ii) MOLECULE TYPE: protein (ix) FEATURE:
(D) OTHER INFORMATION: KHCV E2A, Fig. 2

(xi) SEQUENCE DESCRIPTION: SEQ ID NO:46:

```
Gly Ala Gln Gly Arg Ala Ala Ser Ser Leu Thr Ser Leu Phe Ser Pro
 1               5                  10                  15

Gly Pro Val Gln His Leu Gln Leu Ile Asn Thr Asn Gly Ser Trp His
            20                  25                  30
```

```
Ile Asn Arg Thr Ala Leu Ser Cys Asn Asp Ser Leu Asn Thr Gly Phe
        35                  40                  45

Val Ala Ala Leu Phe Tyr Lys Tyr Arg Phe Asn Ala Ser Gly Cys Pro
 50                  55                  60

Glu Arg Leu Ala Thr Cys Arg Pro Ile Asp Thr Phe Ala Gln Gly Trp
 65                  70                  75                  80

(2) INFORMATION FOR SEQ ID NO:47:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: protein (ix) FEATURE:
        (D) OTHER INFORMATION: KHCV E2E, Fig. 2

(xi) SEQUENCE DESCRIPTION: SEQ ID NO:47:

Thr Arg Gly Glu Arg Cys Asp Leu Glu Asp Arg Asp Arg Ser Glu Leu
 1               5                  10                  15

Ser Pro Leu Leu Leu Ser Thr Thr Glu Trp Gln Val Leu Pro Cys Ser
                20                  25                  30

Phe Thr Thr Leu Pro Ala Leu Ser Thr Gly Leu Ile His Leu His Gln
        35                  40                  45

Asn Ile Val Asp Ile Gln Tyr Leu Tyr Gly Ile Gly Ser Ala Val Val
 50                  55                  60

Ser Phe Ala Ile Lys Trp Glu Tyr Ile Val Leu Leu Phe Leu Leu Leu
 65                  70                  75                  80

Ala Asp Ala (2) INFORMATION FOR SEQ ID NO:48:

(i) SEQUENCE CHARACTERISTICS:
        (A) LENGTH: 392 amino acids
        (B) TYPE: amino acid
        (C) STRANDEDNESS: single
        (D) TOPOLOGY: linear (ii) MOLECULE TYPE: protein (ix) FEATURE:
        (D) OTHER INFORMATION: KHCV NS5-1.2, Fig. 3

(xi) SEQUENCE DESCRIPTION: SEQ ID NO:48:

Thr Gly Met Thr Thr Asp Asn Val Lys Cys Pro Cys Gln Val Pro Ala
 1               5                  10                  15

Pro Glu Phe Phe Thr Glu Val Asp Gly Val Arg Leu His Arg Tyr Ala
                20                  25                  30

Pro Ala Cys Arg Pro Leu Leu Arg Glu Glu Val Val Phe Gln Val Gly
        35                  40                  45

Leu His Gln Tyr Leu Val Gly Ser Gln Leu Pro Cys Glu Pro Glu Pro
 50                  55                  60

Asp Val Ala Val Leu Thr Ser Met Leu Thr Asp Pro Ser His Ile Thr
 65                  70                  75                  80

Ala Glu Thr Ala Lys Arg Arg Leu Ala Arg Gly Ser Pro Pro Ser Leu
                85                  90                  95

Ala Ser Ser Ser Ala Ser Gln Leu Ser Ala Pro Ser Leu Lys Ala Thr
                100                 105                 110

Cys Thr Thr His His Asp Ser Pro Asp Ala Asp Leu Ile Glu Ala Asn
```

-continued

```
                115                 120                 125
Leu Leu Trp Arg Gln Glu Met Gly Gly Asn Ile Thr Arg Val Glu Ser
        130                 135                 140

Glu Asn Lys Val Val Ile Leu Asp Ser Phe Asp Pro Leu Arg Ala Glu
145                 150                 155                 160

Asp Asp Glu Gly Glu Ile Ser Val Pro Ala Glu Ile Leu Arg Lys Ser
                165                 170                 175

Arg Lys Phe Pro Pro Ala Leu Pro Ile Trp Ala Pro Pro Asp Tyr Asn
                180                 185                 190

Pro Pro Leu Leu Glu Ser Trp Lys Asp Pro Asp Tyr Val Pro Pro Val
            195                 200                 205

Val His Gly Cys Pro Leu Pro Pro Thr Lys Ala Pro Pro Ile Pro Pro
        210                 215                 220

Pro Arg Arg Lys Arg Thr Val Val Leu Thr Glu Ser Thr Val Ser Ser
225                 230                 235                 240

Ala Leu Ala Glu Leu Ala Thr Lys Thr Phe Gly Ser Ser Gly Ser Ser
                245                 250                 255

Ala Ile Asp Ser Gly Thr Ala Thr Ala Pro Pro Asp Gln Ala Ser Gly
                260                 265                 270

Asp Gly Asp Arg Glu Ser Asp Val Glu Ser Phe Ser Ser Met Pro Pro
            275                 280                 285

Leu Glu Gly Glu Pro Gly Asp Pro Asp Leu Ser Asp Gly Ser Trp Ser
        290                 295                 300

Thr Val Ser Glu Glu Ala Ser Glu Asp Val Val Cys Cys Ser Met Ser
305                 310                 315                 320

Tyr Thr Trp Thr Gly Ala Leu Ile Thr Pro Cys Ala Ala Glu Glu Ser
                325                 330                 335

Lys Leu Pro Ile Asn Pro Leu Ser Asn Ser Leu Leu Arg His His Asn
                340                 345                 350

Met Val Tyr Ala Thr Thr Ser Arg Ser Ala Gly Leu Arg Gln Lys Lys
            355                 360                 365

Val Thr Phe Asp Arg Leu Gln Val Leu Asp Asp His Tyr Arg Asp Val
        370                 375                 380

Leu Lys Glu Met Lys Ala Lys Ala
385                 390
```

HCV DIAGNOSTIC AGENTS

FIELD OF THE INVENTION

The present invention relates to hepatitis C virus(HCV)-specific epitopes, recombinant proteins comprising one or more of the HCV epitopes and a process for detecting antibodies against hepatitis C virus in a putative serum sample by using said recombinant proteins. More particularly, it pertains to epitopes of HCV core protein and non-structural 3 protein(NS3), and a recombinant protein comprising the same, epitopes of HCV envelope protein and Non-structural 4 protein, and a recombinant protein comprising the same, and epitopes of HCV non-structural 5 protein and a recombinant protein comprising the same; processes for producing the recombinant proteins; an agent for diagnosing antibodies against hepatitis C virus in a putative serum sample, which comprises said recombinant proteins; and a process for diagnosing hepatitis C by using the agent.

BACKGROUND OF THE INVENTION

Hepatitis C virus(HCV) is a primary cause of viral hepatitis which progresses into cirrhosis or hepatocellular carcinoma, and it has been reported that about 70 to 80% of hepatitis caused by blood transfusion is due to said virus (Alter, H. J., et al., *Lancet*, 2, 838–841(1975); and Dienstag, J. L., et al., *Seminar Liver Dis.*, 6, 67–81(1986)). Said virus is one of RNA viruses consisting of one positive RNA strand and produces a polyprotein precursor from an open reading frame(ORF) of the strand(Choo, Q. L., et al., *Science*, 244, 359–362(1989); and, Choo, Q. L., et al., *Proc. Natl. Acad. Sci. USA*, 88, 2451–2455(1991)).

The gene structure of hepatitis C virus is similar to that of flavivirus or pestivirus(Miller, R. H., et al., *Proc. Natl. Acad. Sci. USA*, 87, 2057–2061(1990); and, Muraiso, K., et al., *Biochem. Biophys. Res. Commun.*, 172, 511–516(1991)), and on the basis of said relationship it is presumed that the polyprotein of hepatitis C virus consists of, from N-terminal to C-terminal, core-envelope 1(E1)-envelope 2/non-structural 1 protein(E2/NS1)-non-structural 2 protein(NS2)-non-structural 3 protein(NS3)-non-structural 4 protein (NS4)-non-structural 5 protein(NS5)(Choo, Q. L., et al., *Proc. Natl. Acad. Sci. USA*, 88, 2451–2455(1991); Takamizawa, A., et al., *J. Virol.*, 65, 1105–1113(1991); and Kato, N., et al., *Proc. Natl. Acad. Sci. USA*, 87, 6524–6528 (1990)).

The infection of hepatitis C virus can be diagnosed by detecting hepatitis C viral RNA directly from a blood sample by using polymerase chain reaction(PCR)(Hosoda, K., et al., *Hepatology*, 15, 777–781(1992); Abe, K., et al., *Hepatology*, 15, 690–695(1992); and, Alter, H. J., *Annals of Internal Medicine*, 115, 644–649(1991), whereby the viral RNA can be detected rather early, i.e., within 1 to 2 weeks from the infection; however, such method entails high cost and long time due to the need to analyze numerous samples. Another diagnostic method is to detect antibodies against hepatitis C virus present in the serum sample, e.g., by an enzyme-linked immunoassay using C100-3 protein(see Houghton et al., PCT WO 89/04669; WO 90/11089). Kuo et al. disclosed in Science 244, 362–384(1989) that more than 70% of patients with post-transfusion hepatitis have antibodies against the C100-3 protein.

However, said C100-3 antigen used as an active ingredient for the diagnostic agents reacts only to the antibodies of patients with chronic hepatitis C, not with those of patients with acute hepatitis C at its early stage since the antibodies are not generally produced until 4 to 6 months after the HCV infection. As a result, it often exhibits a false negative during the early stage of the disease(Alber, H. J., et al., *N. Engl. J. Med.*, 321, 1494–1500(1989); Myamura, T., et al., *Proc. Natl. Acad. Sci. USA*, 87, 983–987(1990)); and, further, it often exhibits false positive results in a considerable proportion in the case of hepatitis caused by the autoimmune disease of the patients and not by HCV(McFarlane, I. G., et al., *Lancet*, 335, 754–757 (1990)).

Okamoto et al. disclosed the nucleotide sequences of the cDNA clones including the 5'-terminal region and structural genes encoding the core protein and envelope protein by using the HCV taken from the serum collected from Japanese hepatitis C patients, and compared said sequences with those of HCV extracted from the serum of chimpanzee which was prepared by Chiron Co. in the U.S. From that result, Okamoto et al. discovered the existence of a subspecific hepatitis C virus and the specificity of the antigens derived from Japanese type HCV for preparing vaccines and diagnostic agents against Japanese type HCV(Jpn. *J. Exp. Med.*, 60, 167–177(1990)). Harada et al. further reported in *J. Virol.*, 65, 3015(1991) that, when the core protein encoded in 5'-terminal portion of the structural gene was used as an antigen for diagnosing anti-HCV antibodies which may be present in the samples taken from putative patients, the antibodies could be detected 6 to 8 weeks earlier than the case of using C100-3 protein.

Further, Choo et al. disclosed an improved diagnostic method using a core protein expressed from a core structural gene and C33C protein expressed from NS3 gene(*Br. Med. Bull.*, 46, 423–441(1990)); and, Okamoto et al. employed synthetic polypeptides synthesized by using the nucleotide sequences of a part of core structural gene to diagnose hepatitis C. UBI Co. of the U.S. developed another diagnostic method wherein synthetic polypeptides consisting of 15 to 65 amino acids encoded in core structural gene were employed as antigens for detecting anti-HCV antibodies (wang, C. Y., EP 442394(1991); Hosein, B., et al., *Proc. Natl. Acad. Sci.*, 88, 3647–3651(1991). In addition, Ortho Diagnostic Systems Inc. of the U.S. reported a second generation diagnostic agent having improved sensitivity for anti-HCV antibodies which was prepared by adding core antigen C22-3, NS3 partial protein C33C and NS4 partial protein C200 to the pre-existing first generation diagnostic agent(McHutchison, J. G., et al., *Hepatology*, 15, 19–25 (1992)); and Alter describes that it it is possible to detect anti-HCV antibodies from a serum taken from an HCV patient 15 to 20 weeks after the infection by HCV (*Annals of Internal Medicine*, 115, 644–649(1991)).

The present inventors also disclosed an intrinsic gene structure of Korean type hepatitis C virus(KHCV) different from the American type or Japanese type HCVs; expressed KHCV UBCORE14 protein from KHCV CORE gene, KHCV UB897 protein from KHCV NS3 gene, KHCV 403 protein from KHCV NS5 gene and envelope proteins from KHCV envelope gene in recombinant yeast or *E. coli* cells; confirmed the immunospecificity of the above expressed proteins; reported the process for purifying said proteins; and developed an improved diagnostic method to detect anti-HCV antibodies from a serum taken from a hepatitis C patient with the KHCV antigenic proteins by employing enzyme-linked immunosorbent assay(ELISA) (see Korean Patent Publication No. 93-683)

The present inventors have endeavored to develop HCV diagnostic agents with an improved accuracy and speed over the above agents As a result, there have been unexpectedly discovered several HCV epitopes which react with the antibodies against HCV with a greater sensitivity and accuracy.

SUMMARY OF THE INVENTION

Accordingly, it is a primary object of the present invention to provide said epitopes of improved reactivity with HCV antibodies; and recombinant proteins comprising one or more HCV epitopes.

Another object of the present invention is to provide nucleotide sequences encoding said epitopes or said recombinant proteins; recombinant expression vectors comprising a nucleotide sequence encoding said recombinant protein which can produce, upon its expression, the. recombinant protein comprising one or more HCV epitopes; and a host cell transformed with the recombinant expression vector.

An additional object of the present invention is to provide a process for producing a recombinant protein comprising one or more HCV epitopes, which comprises culturing said host cell transformed with the recombinant expression vector containing a nucleotide sequence encoding said recombinant protein.

A further object of the present invention is to provide a diagnostic agent comprising one or more recombinant proteins which contain one or more HCV epitopes as (an) active component(s) for detecting anti-HCV antibodies in a putative sample; and a diagnostic kit comprising said agent.

A still further object of the present invention is to provide a process for diagnosing HCV infection at its early stage with speed and accuracy by employing said agent or kit.

In accordance with one aspect of the present invention, there are provided HCV epitopes comprising: KHCV NS4E, an epitope of HCV non-structural 4 protein; KHCV E1G, KHCV E2A and KHCV E2E proteins, epitopes of HCV envelope protein; KHCV COREEPI protein, an epitope of HCV core protein; KHCV 518 protein, an epitope of HCV non-structural 3 protein; and, KHCV NS5–1,2 protein comprising an epitope of non-structural 5 protein; and recombinant proteins comprising one or more said epitopes.

BRIEF DESCRIPTION OF THE DRAWINGS

The above and other objects and features-f the present invention will become apparent from the following description of preferred embodiments taken in conjunction with the accompanying drawings, in which:

FIGS. 1A–1B shows the nucleotide sequences encoding the epitope of core protein(COREEPI) and the epitope of non-structural 3 protein (SEQ ID NO:35 and 36, respectively); and the amino acid sequences of the polypeptides encoded therein, respectively (SEQ ID NO:42 and 43, respectively);

FIGS. 2A–B depicts the nucleotide sequences encoding the epitope of NS4 protein(NS4E) and the epitopes of nonstructural 3 protein(E1G, E2A and E2E (SEQ ID NO:37, 38, 39, and 40, respectively)); and the amino acid sequences of the polypeptides encoded therein, respectively (SEQ ID NO:44, 45, 46, and 47, respectively);

FIGS. 3A–B describes the nucleotide sequence encoding KHCV NS5-1.2 protein (SEQ ID NO: 41)and the amino acid sequence of the polypeptide encoded therein (SEQ ID NO:48);

FIG. 8 portrays an expression vector constructed for the purpose of expressing a DNA fragment encoding a portion of an envelope protein in *E. coli* cells;

DETAILED DESCRIPTION OF THE INVENTION

Figure 4:
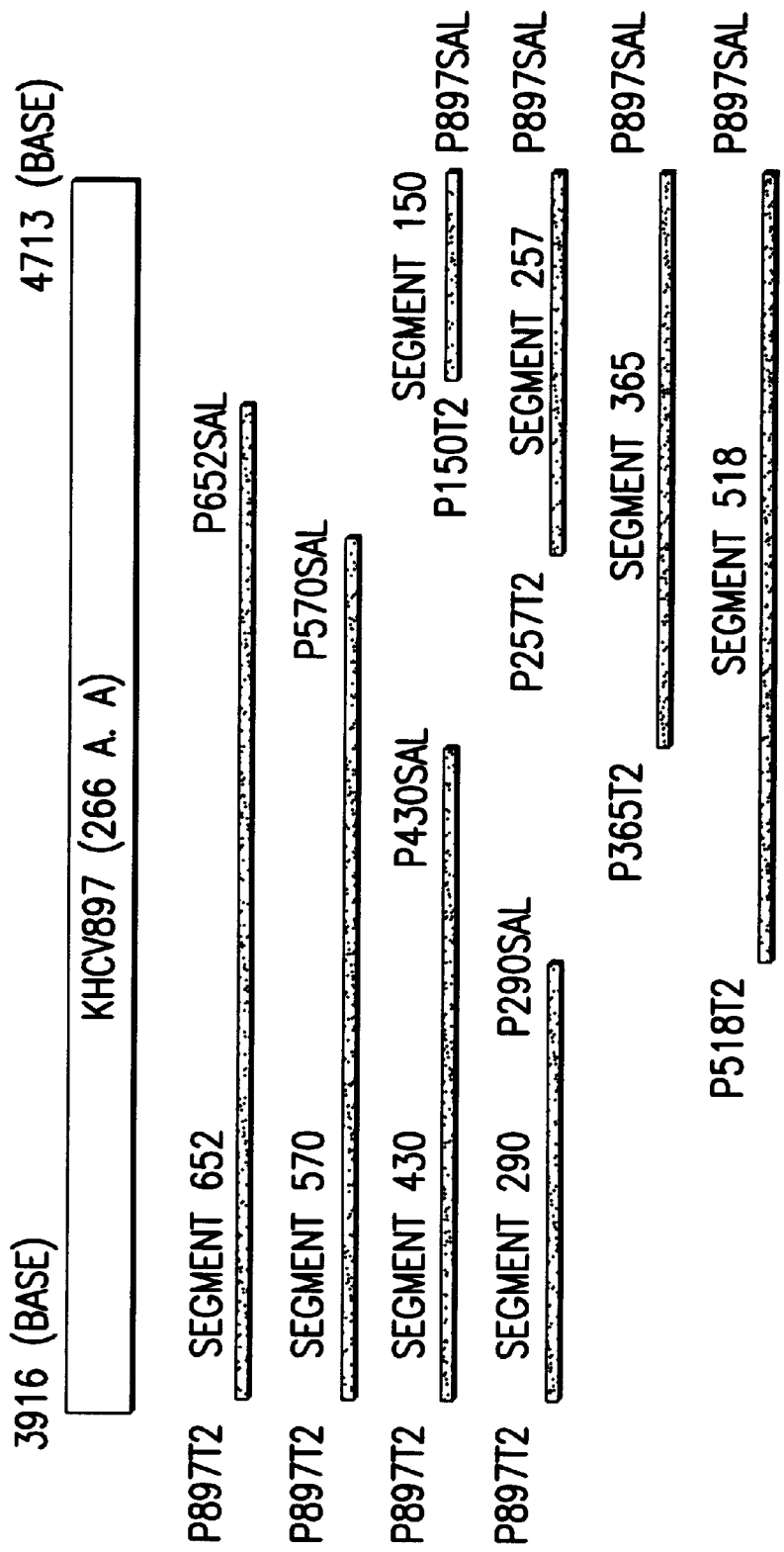
FIG. 4 represents the position of each of the primers used for amplifying the KHCV897 DNA fragment by polymerase chain reaction(PCR)

All references cited herein are hereby incorporated in their entirety by reference.

As used herein, the following terms shall have the following meanings:

The term "hepatitis C virus" refers to a virus causative of non-A non-B hepatitis or hepatitis C. The terms HCV and hepatitis C are used interchangeably herein.

The term "Korean-type hepatitis C virus" or "KHCV" refers to a novel type of HCV which is isolated from Korean hepatitis C patients; and whose cDNA has an open reading frame of a nucleotide sequence encoding the amino acid sequence, wherein the amino acids having the numbers of 842, 849 and 853 are phenylalanine, leucine and threonine; or leucine, phenylalanine and alanine, respectively.

The term "epitope" refers to an antigenic determinant of a polypeptide which is capable of eliciting an immune response in an immunologically competent host organism and/or is capable of specifically binding itself to a complementary antibody. An epitope in accordance with the present invention generally consists of at least 6 amino acids, preferably 7 or 8 amino acids.

Other terms used herein have the normal and conventional meanings as practiced and understood in the art.

Hereinafter, the number of a nucleic acid of an HCV cDNA or of an amino acid of an HCV protein is based on the full KHCV nucleotide sequence or amino acid sequence disclosed in Korean Patent Laid-open Publication No. 93-683.

The present invention will now be more specifically illustrated hereinbelow.

1. Determination of Epitopes

The information on nucleotide sequences of cDNAs of HCV, for example, KHCV(KHCV-LBC1, which was deposited at American Type Culture Collection(ATCC) on May 14, 1991 with the accession number of ATCC 75008; Korean Patent Laid-open Publication No. 93-683), is used to synthesize primers for polymerase chain reaction which correspond to the 5'- and the 3'-ends of cDNA fragments encoding KHCV897 protein, envelope protein, or non-structural 5 protein.

A polymerase chain reaction is carried out by using said primers and KHCV897 gene(which was deposited at ATCC on Jun. 27, 1991 with the accession number of ATCC 68640), KHCV envelope 1 gene(which was deposited at ATCC on Dec. 11, 1991 with the accession number of ATCC 68878), KHCV envelope 2 gene(which was deposited at ATCC on Dec. 11, 1991 with the accession numbers of ATCC 69866 and ATCC 74117) and KHCV NS5 gene (Korean Patent Laid-open Publication No. 93–683) as templates to obtain cDNA fragments of KHCV897 gene, KHCV envelope 1 and 2 gene, and KHCV NS5 gene. Each cDNA fragment is inserted into a vector, and the expression vector is used to transform a suitable host organism such as *E. coli*. The polypeptides produced by the transformed host cells are subjected to an electrophoresis on polyacrylamide gel and then to a western blotting analysis by using a serum taken from a hepatitis C patient to confirm which polypeptides react specifically with anti-KHCV antibodies as epitopes of KHCV antigens. The location of the confirmed epitopes in full sequence of KHCV cDNA is also examined.

As a result, it has been found that the epitope of KHCV897 protein exists in the carboxyl end of KHCV897 protein which is expressed from the 366 base pairs corresponding to from the 4348th to the 4713rd nucleotides of KHCV cDNA(see FIG. 4 for the amino acid and nucleotide sequence of epitope of KHCV897 protein).

In case of envelope proteins, epitopes are found to exist in the carboxyl terminal of KHCV envelope 1 protein which is expressed from the 309 base pairs corresponding to from the 1201st to the 1509th nucleotides of KHCV cDNA(E1G protein); in the amino terminal of KHCV envelope 2 protein which is expressed from the 240 base pairs corresponding to from the 1510th to the 1749th nucleotides of KHCV cDNA (E2A protein); and in the carboxyl terminal of KHCV envelope 2 protein which is expressed from the 249 base pairs corresponding to from the 2281st to the 2529th nucleotides of KHCV cDNA(E2E protein)(see FIGS. 2A–B for the amino acid and nucleotide sequences of E1G, E2A and E2E proteins).

In addition, epitopes of NS5 protein exists in the amino terminal of NS5 protein encoded by 1,200 base pairs corresponding to from 6649th to 7824th nucleotides including KHCV403 CDNA fragment and reacts specifically with a serum taken from a KHCV patient with a higher sensitivity than KHCV403.

2. Recombinant Proteins Comprising One or More HCV Epitopes

Epitopes of HCV antigens are very important for the development of efficient and economical diagnostic agents and vaccines. In particular, the fusion proteins comprising one or more epitopes are more preferable in terms of economy, efficiency and accuracy; and the fusion proteins comprising more than one epitope are most preferable.

As a HCV recombinant protein comprising more than one HCV epitope, there may be included, preferably, a recombinant CORE 518 fusion protein comprising the epitopes of KHCV core and NS3 proteins, and a recombinant NS4E1E2 fusion protein comprising the epitopes of KHCV E1, E2 and NS4 proteins.

The recombinant proteins may be prepared by employing various expression vector systems containing a nucleotide sequence encoding said fusion protein; and, the vector may be capable of directing production of a recombinant fusion protein comprising said fusion protein and other specific protein, preferably, ubiquitin which can increase the protein stability or facilitate the purification procedure.

For instance, a desired HCV protein can be obtained by expressing a fused polynucleotide of a HCV cDNA fragment and ubiquitin gene in bacteria such as *Escherichia coli*, and then excising the ubiquitin in vitro by a ubiquitinase named UBP 1 (Tobias, J. W. et al., *J. Biol. Chem.*, 266, 12021–12028 (1991)). The recombinant fusion protein comprising ubiquitin as well as the KHCV fusion protein can be used in accordance with the invention as long as it retains the necessary characteristic of KHCV protein, e.g., antigenicity of HCV.

The above expression system may be effectively employed where the desired protein is unstable and can be digested easily by proteinases in a host cell since the ubiquitin can protect the desired protein from the protease attack or stabilize it. Moreover, the expression of desired recombinant protein fused with ubiquitin can be confirmed by using anti-ubiquitin antibodies and easily purified by using the properties of ubiquitin.

For the purpose of obtaining a desired HCV protein comprising HCV epitopes, a compatible host cell is transformed with an expression vector containing an HCV cDNA fragment encoding HCV epitopes; and the transformed cell is cultured under a condition that allows the expression.

Selection of an appropriate host organism is affected by a number of factors as well known in the art. These factors include, for example, compatibility with the chosen vector, toxicity of the proteins encoded by the recombinant plasmid, ease of recovery of the desired protein, protein characteristics, biosafety and costs. A balance of these factors must be considered, it is being understood that not all hosts will be equally effective for the expression of a particular recombinant DNA molecule.

Suitable host organisms which may be used in the invention include, but are not limited to, bacteria such as *Escherichia coli* and yeasts such as *Saccharomyces cerevisiae*.

The polypeptides produced in a host cell may be isolated and purified by a combined use of conventional methods, e.g., cell disruption, centrifugation, dialysis, salting-out, chromatography, gel filtration, electrophoresis and electroelution.

The polypeptides of the invention can also be chemically synthesized by a suitable method such as exclusive solid phase synthesis, partial solid phase method, fragment condensation or classical solution synthesis. The method of solid phase synthesis disclosed by Merrifield(*J. Am. Chem. Soc.*, 85, 2149(1963)) is preferred.

Figure 5:
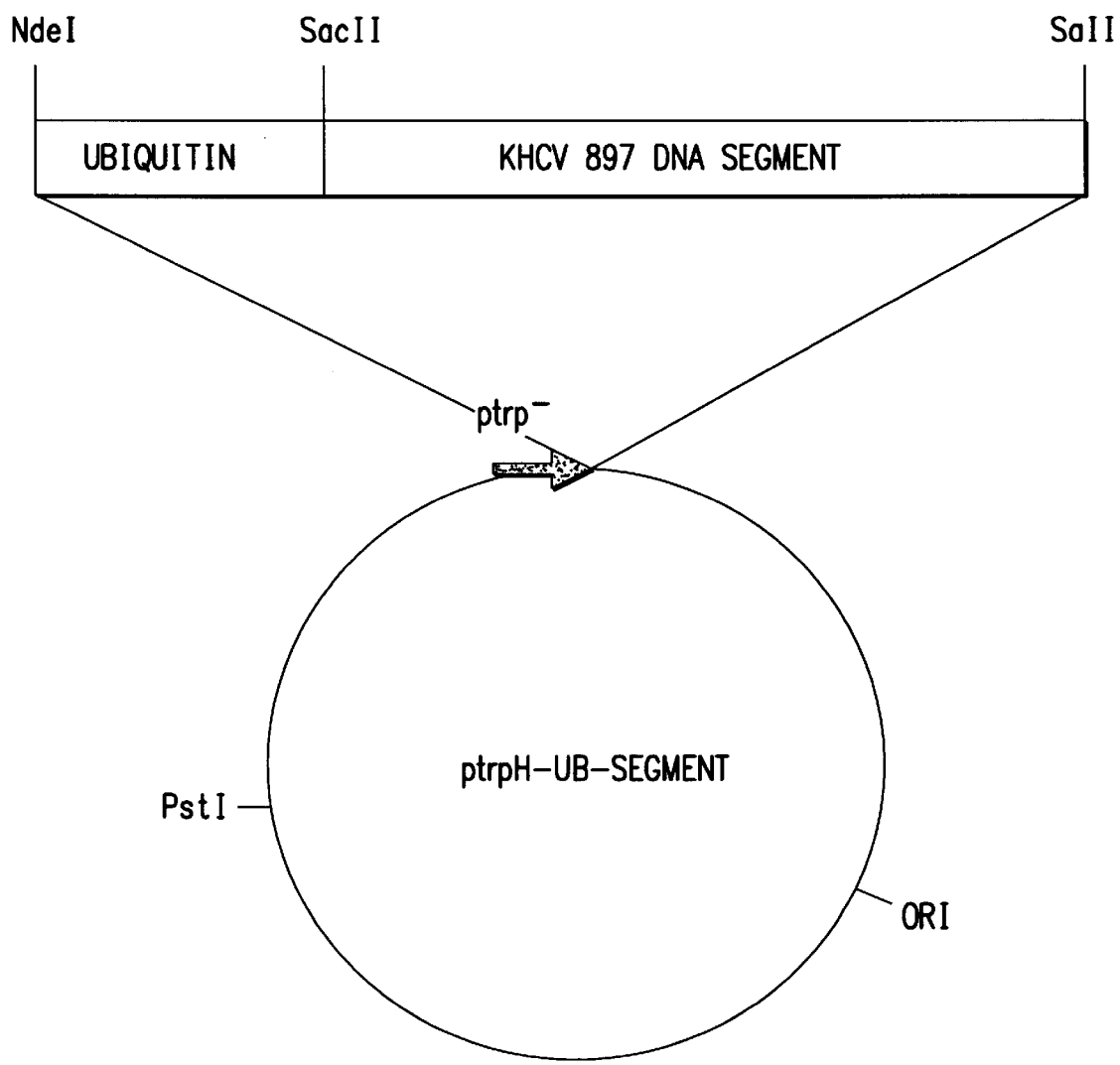
FIG. 5 describes an expression vector constructed for the purpose of expressing a KHCV897 DNA fragment in *Escherichia coli* cells.

On the other hand, amino acid substitutions in proteins which do not substantially alter biological and immunological activities have been known to occur and have been described, e.g., by Neurath et al., in The Proteins, Academic Press, New York(1979), in particular in FIG. 5 appearing on page 14 thereof. Such functionally equivalent amino acid substitutions are believed to fall within the scope of the invention as long as the resulting proteins retain the same antigenic properties.

In this specification, standard three-letter abbreviations are used to represent nucleotides and amino acids. The meanings of these abbreviations can be found in standard biochemistry textbook, e.g., Lehninger, *Principles of Biochemistry*, Worth Publishers Inc., New York, pp. 96, 798(1984).

1) Preparation of CORE518 protein

The information on nucleotide sequences of cDNAs of Korean type hepatitis C virus(see Korean Patent Laid-open Publication No. 93-683) was used to synthesize primers for polymerase chain reaction which correspond to the 5'- and the 3'-ends of KHCV518 cDNA fragment encoding KHCV518 protein, which comprises the epitope of KHCV NS3 protein. A primer corresponding to the 5'-end of cDNA is designed to have recognition site of endonuclease in its the 5'-end so as to ligate with the 3'-end of COREEPI gene encoding epitope of core protein, and a primer corresponding to the 3'-end of cDNA is designed to have a termination codon and recognition site of endonuclease. Therefore, said primers allow the synthesis of fusion protein to start from the initiation codon of ubiquitin and then end at the inserted termination codon, and facilitates the cloning of the fused gene into the expression vector.

Moreover, it is possible to arrange said genes encoding said two epitopes in an opposite order by regulating the sequence of the primers properly, and it is also possible to insert other amino acid sequences between the two epitopes as long as the resulting proteins retain the same antigenic properties.

A polymerase chain reaction is carried out by using said primers and KHCV897 gene(which was deposited at ATCC on Jun. 27, 1991 with the accession number of ATCC 68640) as a template to amplify KHCV518 gene, and the gene fragment obtained by digesting said KHCV518 gene with restriction endonucleases is inserted into a plasmid ptrp-UB-CORE14 in place of part of KHCV Core14 gene exclusive of COREEPI gene to obtain an expression vector thereof. The expression vector is used to transform suitable host organisms such as *E. coli*. The polypeptides produced by the transformed host cell are subjected to an electrophoresis on 15% polyacrylamide gel and then to a western blotting analysis by using a serum taken from a hepatitis C patient to confirm that the CORE518 protein reacts specifically with anti-KHCV antibodies.

2) Preparation of NS4E1E2 protein

The information on nucleotide sequences of cDNAs of Korean type hepatitis C virus(see Korean Patent Laid-open Publication No. 93-683) is used to ligate the nucleotide sequences encoding the epitope of NS4 protein(NS4E) and the epitopes of envelope proteins(E1G, E2A and E2E), for example, by using polymerase chain reaction with appropriate primers. First of all, primers for PCR which correspond to the 5'- and 3'-ends of nucleotide sequence encoding E1E2 protein, which comprises the epitopes of envelope proteins, i.e., E1G, E2A and E2E . A primer corresponding to the 5'-end of said nucleotide sequence is designed to have 21 nucleotides the same as those in the 3'-end of NS4 gene in its the 5'-end so as to ligate with the 3'-end of NS4 gene, and a primer corresponding to the 3'-end of cDNA is designed to have a termination codon and recognition site of endonuclease. Therefore, said primers allow the synthesis of fusion protein to start from the initiation codon of ubiquitin and then end at the inserted termination codon, and facilitates the cloning of the fused gene into the expression vector.

Moreover, it is possible to arrange said four genes encoding the respective epitopes in an optional order by regulating the sequence of the primers properly, and it is also possible to insert other amino acid sequences between any two epitopes as long as the resulting proteins retain the same antigenic properties.

Figures 16A, 16B:
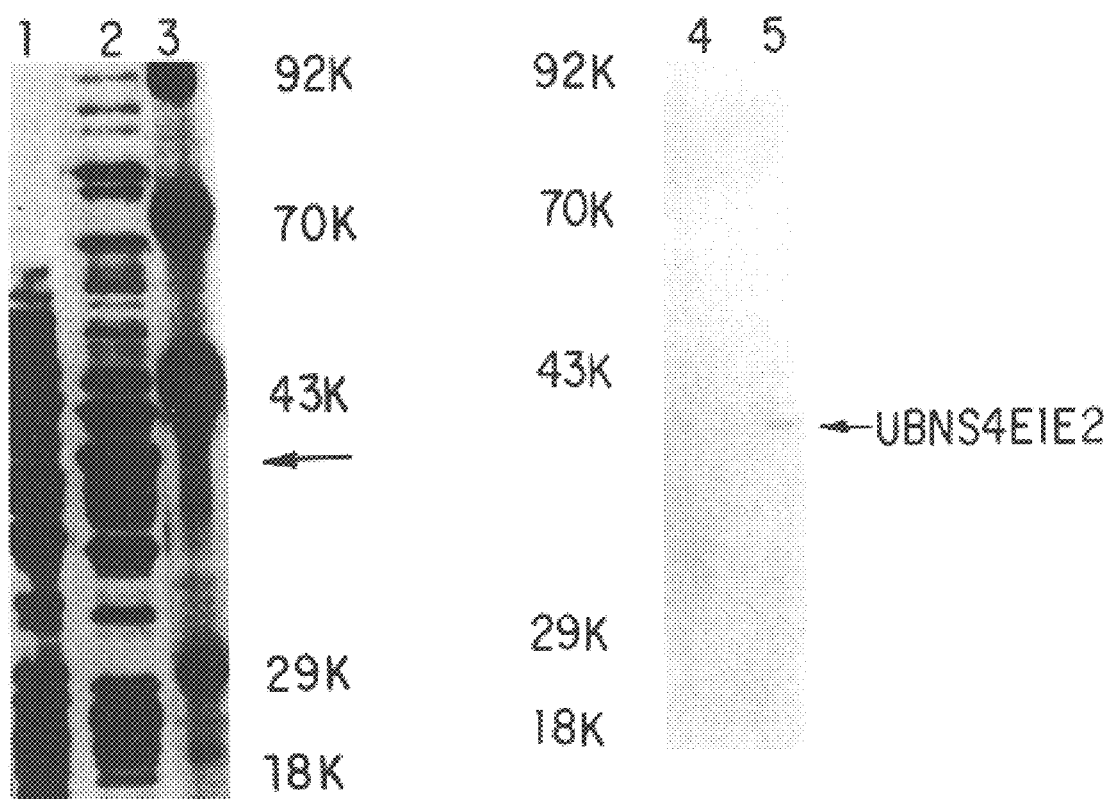
FIG. 16A shows the result of SDS polyacrylamide gel electrophoresis(SDS-PAGE) after the expression of the recombinant DNA encoding UBNS4E1E2 protein in *E. coli* cells.
FIG. 16B shows the result of western blotting analysis of the gel of FIG. 16A by using a serum taken from a hepatitis C patient.
Figure 17:
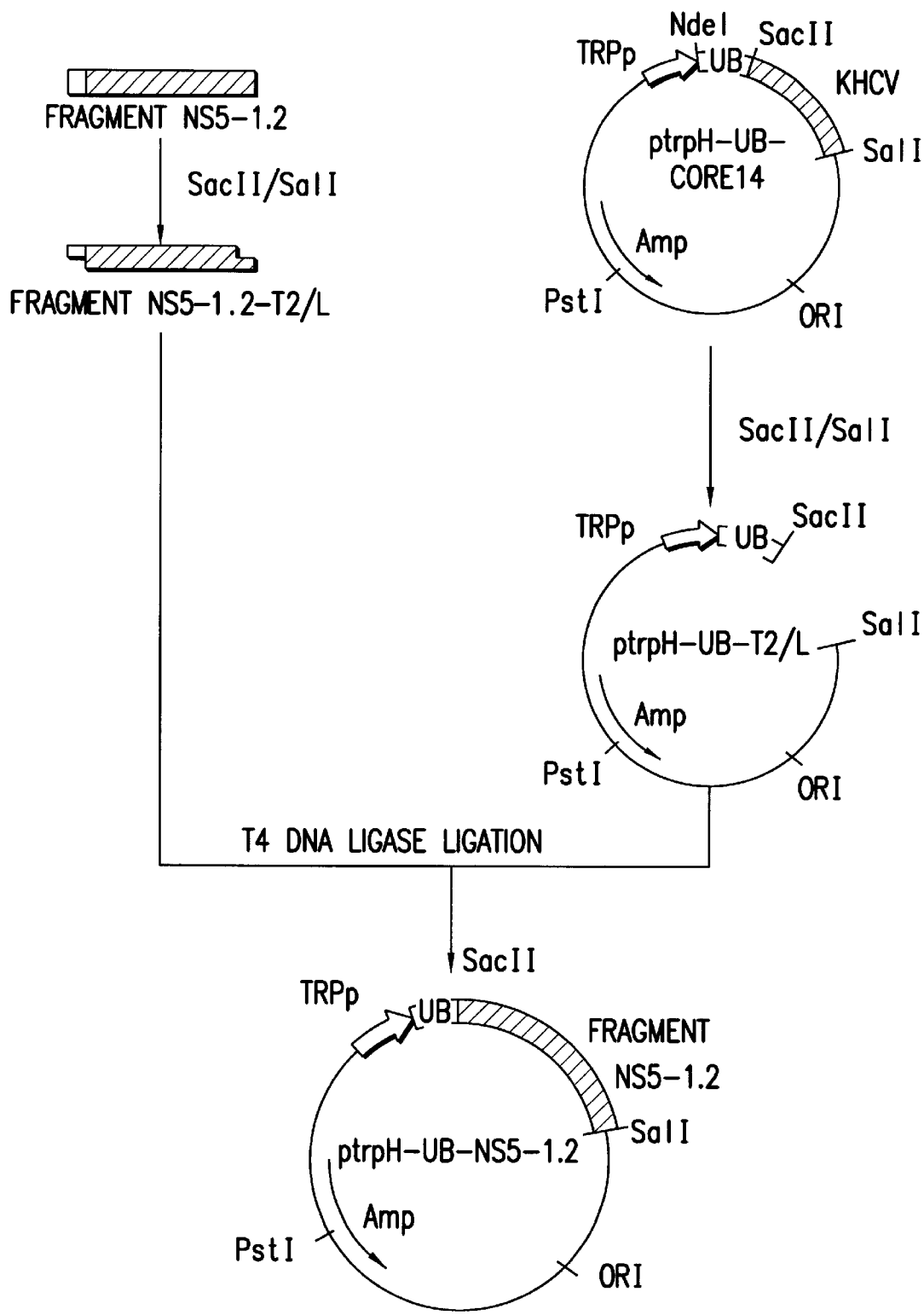
FIG. 17 shows a schematic diagram for preparing an expression vector constructed for the purpose of expressing a recombinant DNA encoding UBNS5-1.2 protein comprising ubiquitin and NS5-1.2 protein.
Figure 18A:
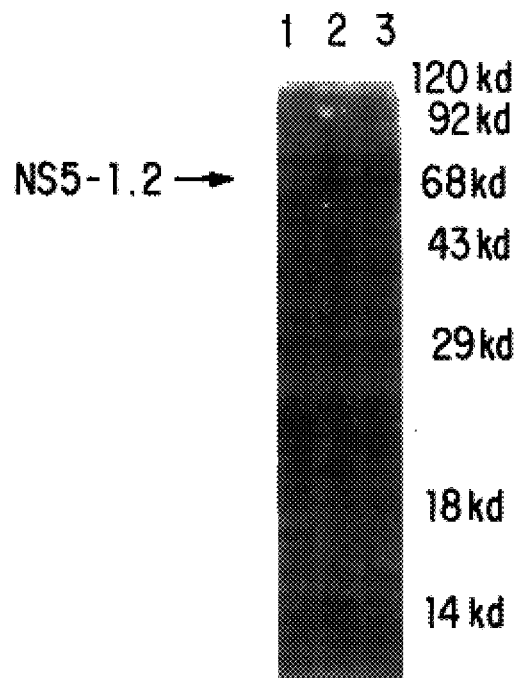
FIG. 18A shows the result of SDS polyacrylamide gel electrophoresis(SDS-PAGE) after the expression of the recombinant DNA encoding UBNS5-1.2 protein in *E. coli* cells.
Figure 18B:
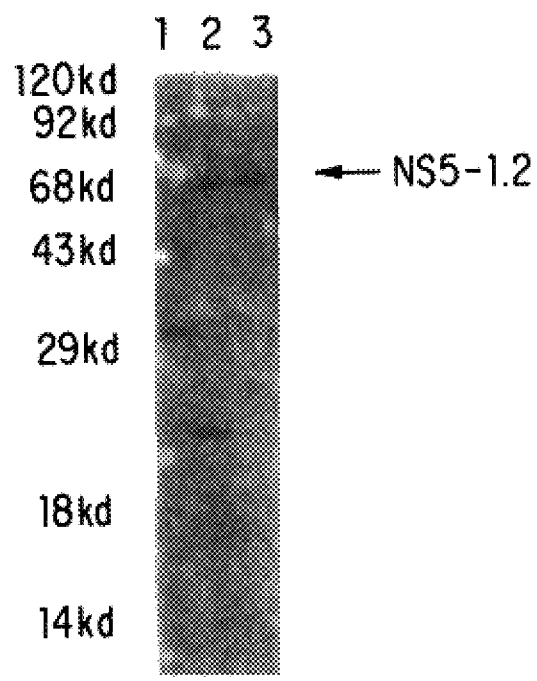
FIG. 18B shows the result of western blotting analysis with the gel of FIG. 18A by using a serum taken from a hepatitis C patient.
Figure 19A:
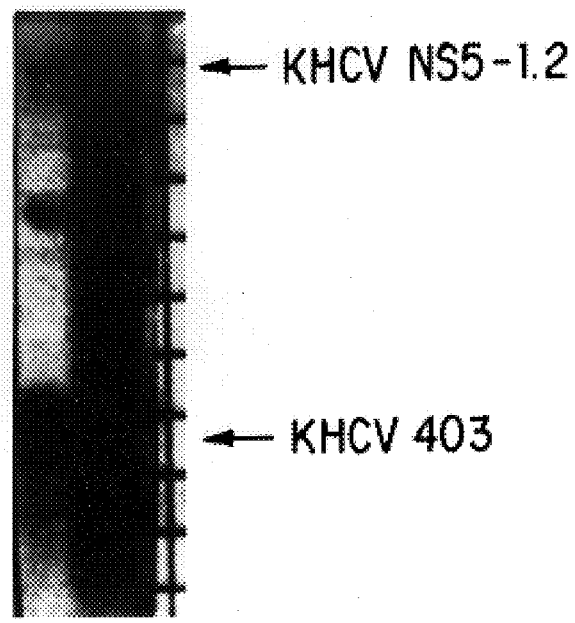
FIG. 19A shows the result of SDS polyacrylamide gel electrophoresis(SDS-PAGE) after the expression of KHCV403 protein and recombinant UBNS5-1.2 protein in *E. coli* cells.
Figure 19B:
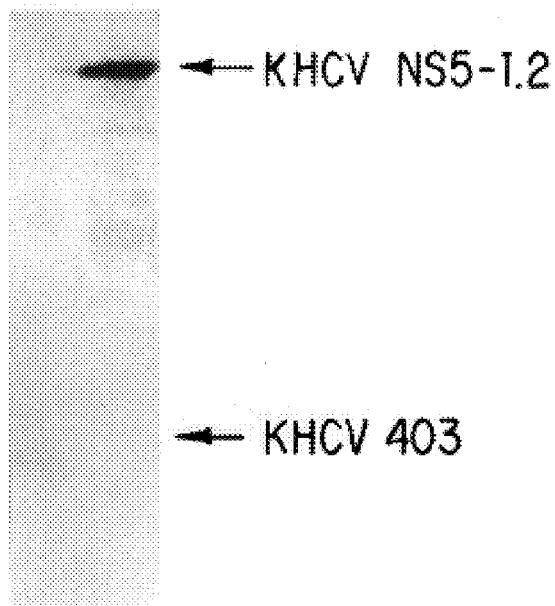
FIG. 19B shows the result of western blotting analysis with the gel of FIG. 19A by using a serum taken from a hepatitis C patient.

A polymerase chain reaction is carried out by using said primers and plasmid ptrpH-UB-E1E2(see FIG. 16) as a template to amplify E1E2 gene. A second polymerase chain reaction is carried out by using E1E2 and NS4 gene as templates to amplify NS4E1E2 gene, and the gene fragment obtained by digesting said NS4E1E2 gene with restriction endonucleases is inserted into a plasmid ptrp-UB-CORE14 in place of KHCV Core14 gene to obtain an expression vector thereof. The expression vector is used to transform suitable host organisms such as *E. coli* W3110(ATCC 37339), and the transformed host cell is cultured under a condition that allows the expression The polypeptides produced by the transformed host cell are subjected to electrophoresis on 15% polyacrylamide gel and then to a western blotting analysis by using a serum taken from a hepatitis C patient to confirm that the NS4E1E2 protein reacts specifically with anti-KHCV antibodies.

3) Preparation of NS5–1.2 protein

The information on nucleotide sequences of cDNAs of Korean type hepatitis C virus(see Korean Patent Laid-open Publication No. 93-683) is used to synthesize primers for polymerase chain reaction which correspond to the 5'- and 3'-ends of NS5-1.2 cDNA fragment encoding NS5-1.2 protein. A primer corresponding to the 5'-end of cDNA is designed to have a recognition site of endonuclease in its the 5'-end so as to ligate with the 3'-end of ubiquitin gene, and a primer corresponding to the 3'-end of cDNA is designed to have termination codon and recognition site of endonuclease. Therefore, said primers allow the synthesis of fusion protein to start from the initiation codon of ubiquitin and then end at the finished by inserted termination codon, and facilitates the cloning of the fused gene into the expression vector.

A polymerase chain reaction is carried out by using said primers and KHCV-LBC1 gene(which was deposited at ATCC on May 14, 1991 with the accession number of ATCC 75008; see Korean Patent Laid-open Publication No. 93-683) as a template to amplify NS5-1.2 gene, and the gene fragment obtained by digesting said NS5-1.2 gene with restriction endonucleases is inserted into a plasmid ptrp-UB-CORE14 in place of KHCV Core14 gene to obtain an expression vector thereof. The expression vector is used to transform suitable host organisms such as E. coli. The polypeptides produced by the transformed host cell are subjected to an electrophoresis on 15% polyacrylamide gel and then to a western blotting analysis by using a serum taken from a hepatitis C patient to confirm that the NS5-12 protein reacts specifically with anti-KHCV antibodies.

3. Preparation of Diagnostic agent for hepatitis C comprising mixed HCV antigen polypeptides The diagnostic agent in accordance with the present invention comprises one or more HCV epitopes including KHCV NS 4E, KHCV E1G, KHCV E2A, KHCV E2E, COREEPI, KHCV 518 and KHCV NS5–1.2, and/or recombinant proteins comprising one or more of said epitopes.

Further, the present invention provides a hepatitis C diagnostic kit which comprises the necessary agents to carry out the above procedure, essentially consisting of a diagnostic agent containing KHCV polypeptide(s) which carries one or more KHCV epitopes.

Preferably, it comprises a recombinant CORE518 fusion protein comprising the epitopes of KHCV core and NS3 proteins, a recombinant NS4E1E2 fusion protein comprising the epitopes of KHCV E1, E2 and NS4 proteins, and/or a recombinant NS5-1.2 protein.

When the diagnostic agent comprises more than one recombinant protein comprising HCV epitope(s) in a mixture, the proportion of each protein may be optionally adjusted, although it is generally preferable to use each protein in an equal molar amount.

The novel diagnostic method in accordance with the present invention comprises the following steps:

(i) a diagnostic agent containing one or more KHCV polypeptides is added to a solid support, e.g., a well of microtiter plate to make said KHCV antigen adsorb onto the surface of the well;

(ii) a putative sample diluted with a diluent is added to the antigen-coated well where the antigen-antibody complex is to be formed should there be any anti-KHCV antibodies in the serum;

(iii) an enzyme, e.g., HRP(horseradish peroxidase) conjugated anti-human IgG antibody is added to the well to allow the anti-human IgG antibody-HRP to bind the antibodies of the complex formed in step(ii); and (iv) substrates for the enzyme, e.g., O-phenylene diamine dihydrochloric acid(OPD) and hydrogen peroxide for peroxidase are added to the well to develop a color reaction. When the putative serum contains anti-KHCV antibodies, color appears as a result of the reaction of the enzyme with the substrates. The color reaction is stopped by an addition of diluted sulfuric acid.

The degree of color intensity can be measured with a microwell reader; and the existence of anti-HCV antibodies can be determined on the basis of the result. The solid support for the diagnostic method may be of polystyrene beads or nitrocellulose strips.

In case that the recombinant protein(s) of the present invention which comprises more than one KHCV epitope is used for preparing a diagnostic agent, it would allow a more economical and accurate diagnosis than a case using any of the existing HCV antigens with only one epitope in a mixture. Moreover, the diagnostic agent and diagnostic kit of the present invention which comprise a mixture of recombinant proteins comprising KHCV epitopes show an excellent diagnostic result.

The following Examples are intended to further illustrate the present invention without limiting its scope; and the experimental methods used in Examples are practiced in accordance with Reference Examples given hereinbelow, unless otherwise stated.

Further, percentages given below for solids in solid mixtures, liquids in liquids and solids in liquids are on a wt/wt, vol/vol and wt/vol basis, respectively, unless specifically defined otherwise.

REFERENCE EXAMPLE 1

Digestion of DNA with Restriction Endonuclease

In a sterilized 1.5 ml eppendorf tube were added restriction endonuclease and reaction buffers to be a reaction volume ranging from 50 to 10 $\mu$l, and the reaction was carried out at a temperature of 37° C. for 1 to 2 hours. When the reaction was completed, the reaction mixture was heat-treated at 65° C. for 15 minutes(or extracted with phenol and precipitated with ethanol in the case of a heat-resistant endonuclease) to inactivate the restriction endonuclease.

Restriction enzymes and reaction buffers used in this example were purchased from NEB(New England Biolabs, Jolla, Mass., U.S.A.).

10× reaction buffer for the reaction of a restriction endonuclease has the following composition:

10× NEB reaction buffer 1: 100 mM bis Tris propane-HCl, 100 mM $MgCl_2$, 10 mM dithiothreitol(DTT), pH 7.0

10× NEB reaction buffer 2: 100 mM Tris-HCl, 100 mM $MgCl_2$, 500 mM NaCl, 10 mM DTT, pH 7.0

10× NEB reaction buffer 3: 100 mM Tris-HCl, 100 mM $MgCl_2$, 1000 mm NaCl, 10 mM DTT, pH 7.0

10× NEB reaction buffer 4: 200 mM Tris-acetate, 100 mM magnesium acetate, 500 mM potassium acetate, 10 mM DTT, pH 7.0

REFERENCE EXAMPLE 2

Phenol Extraction and Ethanol Precipitation

After the completion of an enzyme reaction with DNA, the reaction mixture was extracted with phenol for the purpose of inactivating the enzyme or recovering the DNA in the reaction mixture, wherein phenol preequilibrated with a buffer containing 10 mM Tris-HCl(pH 8.0) and 1 mM EDTA was used.

Phenol extraction was carried out by mixing equal volumes of the sample and the phenol with vigorous shaking; centrifuging the mixture at 15,000 rpm for 5 minutes; and transferring the aqueous layer into a new tube. The above procedure was repeated three times.

The aqueous layer was, then, extracted with an equal volume of chloroform(chloroform:isobutanol=24:1) and the aqueous layer was separated again; 0.1 volume of 3M sodium acetate and 2.5 volume of absolute ethanol were added thereto; and, the mixture was centrifuged at 15,000 rpm and 4° C. for 20 minutes after having left it at −70° C. for 30 minutes or at −20° C. for over 12 hours, to recover the nucleic acid.

REFERENCE EXAMPLE 3

Ligation Reaction

Ligation reaction of DNA was carried out by employing T4 DNA ligase and 10x ligation reaction buffer(0.5M Tris- HCl, pH 7.0, 0.1M MgCl$_2$, 0.2M DTT, 10 mM ATP, 0.5 mg/ml bovine serum albumin(BSA)) purchased from NEB. The reaction volume was generally 20 μl, and 10 units of T4 ligase was used for the ligation of cohesive ends of DNA, while 100 units was used for the ligation of blunt ended DNAs.

The reaction was carried out at 16° C. for 5 hours or at 4° C. for over 14 hours; and, after the reaction was completed, the reaction mixture was heated at 65° C. for 15 minutes to inactivate T4 DNA ligase.

REFERENCE EXAMPLE 4

Transformation of *E. coli*

Transformation of *E. coli* strains(e.g., *E. coli* HB101 (ATCC 33694), *E. coli* W3110(ATCC 27325) or *E. coli* JM105(ATCC 47016)) was carried out by employing a method known in the art, e.g., as described by Maniatis et al., in Molecular Cloning: A Laboratory Manual, Cold Spring Harbor Press, N.Y. (1982), or by Cohen in Proc. Natl. Acad. Sci. U.S.A. 69, 2110(1972).

REFERENCE EXAMPLE 5

Synthesis of Oligonucleotides

Oligonucleotides were synthesized by employing a DNA synthesizer(Applied Biosystems Inc., model No. 380B, U.S.A.) using automatic solid phase phosphoamidite chemistry.

The synthesized oligonucleotides were purified by using denaturing polyacrylamide gel(2M urea, 12% acrylamide and bis(29:1), 50 mM Tris, 50 mM boric acid, 1 mM EDTA-Na$_2$) electrophoresis and C$_{18}$ SEP-PAK(Waters Inc., U.S.A) column chromatography by using acetonitrile.water (50:50) as an eluent; and the amount was determined by measuring O.D. at 260 nm.

REFERENCE EXAMPLE 6

Polymerase Chain Reaction(PCR)

To a mixture of 10 to 100 ng of a template DNA, 10 μl of 10x Taq polymerase reaction buffer(10 mM Tris-HCl, pH 8.3, 500 mM KCl, 15 mM MgCl$_2$, 0.1%(w/v) gelatin), 10 μl of a mixture of dNTP's(each of dGTP, dATP, TTP and dCTP is 10 mM), 2 μg of each primer(generally, 2 primers were used for a reaction, and in the case that 3 primers were used, the primer located in the middle was used in an amount of 0.02 μg), and 0.5 μl of AmpliTaq DNA polymerase(Perkin Elmer Cetus, U.S.A.) was added distilled water in an amount to make a-total volume of 100 μl; and 50 μl of mineral oil was added thereto to protect the reaction mixture from evaporation.

The PCR was carried out by using a thermal cycler(Perkin Elmer Cetus, U.S.A.); and the thermal cycle was programmed to repeat 25 times or more, the cycle of: 95° C. for 1 minute → 55° C. for 1 minute → 72° C. for 2 minutes, and, finally, the reaction was carried out at 72° C. for 10 minutes.

After the reaction was completed, the mixture was extracted with phenol and the PCR products were recovered by precipitation with ethanol; and, the precipitate was dissolved in 20 μl of TE buffer solution(10 mM Tris-HCl, 1 mM EDTA, pH 7.5).

REFERENCE EXAMPLE 7

Preparation of HRP-Conjugated Anti-Human IgG Antibodies

Antibodies against the Fc region of human IgG (Immunovision Inc., Arizona, U.S.A., Cat. No. GHF-1001) were purified by chromatography using human IgG-attached sepharose CL-4B affinity column and protein-G column (Pharmacia LKB, Sweden) to obtain said antibodies with a purity over 90%. The obtained antibodies were labelled with horseradish peroxidase according to sodium periodate method described in Nakane, et al., J. Histochemcytochem. 22, 1084(1974) as follows:

To a solution of 5 mg of horseradish peroxidase (Boehringer Mannheim, Germany, Cat. No. 814.393) dissolved in 1.2 ml of distilled water(DW) was added 0.3 ml of 0.1M sodium periodate solution in 10 mM sodium phosphate buffer(pH 7.0); and the mixture was reacted at room temperature for 20 min. The resulting solution was dialyzed against 1 mM sodium acetate buffer for 16 hours.

1.5 ml of the resulting peroxidase solution was mixed with 1 ml of 20 mM sodium carbonate solution(pH 9.5) in which purified antibodies were dissolved to a concentration of 10 mg/ml, and the mixture was reacted at room temperature for 2 hours. Then, 100 μl of solution of sodium borohydride in DW (4 mg/ml) was added thereto to remove the unreacted Schiff's base by a reduction reaction. The resulting solution was dialyzed against phosphate buffered saline overnight and then passed through sephadex G-200 column to remove free antibodies or peroxidases.

Example 1

Determination of Epitope of Non-Structural 3 Protein

<Step 1> Amplification of partial fragments of KHCV 897 DNA (1-1) Preparation of primers In order to amplify partial fragments of KHCV 897 DNA encoding non-structural 3 protein and to clone each into an expression vector comprising ubiquitin gene under the control of trp promotor, the following primers were synthesized:

Primer P897T2 (SEQ ID NO: 1): 5'-TGAGACTCCGCGG TGGTGCGGTGGAATTCATACCCGTT-3' comprising a-recognition site of SacII and the 3916th to the 3936th nucleotides of KHCV-LBC1;

Primer P518T2 (SEQ ID NO: 2): 5'-TGAGACTCCGCGG TGGTATCACCACAGGFCGCCCCTATC-3' comprising a recognition site of SacII and the 4195th to the 4216th nucleotides of KHCV-LBC1;

Primer P365T2 (SEQ ID NO: 3): 5'-TGAGACTCCGCGG TGGTGCGGAGACGGCTGGAGCGCGG-3' comprising a recognition site of SacII and the 4348th to the 4369th nucleotides of KHCV-LBC1;

Primer P257T2 (SEQ ID NO: 4): 5'-TGAGACTCCGCGG TGGTAACATTGGAGAGATTCCTTTC-3' comprising a recognition site of SacII and the 4447th to the 4468th nucleotides of KHCV-LBC1;

Primer P150T2 (SEQ ID NO: 5): 5'-TGAGACTCCGCGG TGGTTTGTCCCTCGGAGTCAATGCT-3' comprising a recognition site of SacII and the 4564th to the 4585th nucleotides of KHCV-LBC1;

Primer P897SAL (SEQ ID NO: 6): 5'-GACTGGACTAT TAACACGTATTACAGTCGATCAC-3' comprising a stop codon to terminate translation after the 4712nd nucleotide of KHCV-LBC1 and a recognition site of SalI;

Primer P652SAL (SEQ ID NO: 7): 5'-GACTGGACTATTA CAGCTTTGCAGCGAGCTCGTC-3' comprising a stop codon to terminate translation after the 4562nd nucleotide of KHCV-LBC1 and a recognition site of SalI;

Primer P570SAL (SEQ ID NO: 8): 5'-GACTGGACTATT AGAGGGGGATGGCTTTGCCATA-3' comprising a stop codon to terminate translation after the 4487th nucleotide of KHCV-LBC1 and a recognition site of SalI;

Primer P430SAL (SEQ ID NO: 9): 5'-GACTGGACTAT TATTGGTCCAGGACCGTGCCAAT-3' comprising a stop codon to terminate translation after the 4346th nucleotide of KHCV-LBC1 and a recognition site of SalI; and Primer P290SAL (SEQ ID NO: 10): 5'-GACTGGACTAT TAGGCGCCTGTGGTGATGGTCCT-3' comprising a stop codon to terminate translation after the 4208th nucleotide of KHCV-LBC1 and a recognition site of SalI.

(1-2) Polymerase chain reaction 8 different test tubes were prepared, which were provided with the primers as follows.

Tube A: Primer P897T2 2 $\mu$g, Primer P652SAL 2 $\mu$g
Tube B: Primer P897T2 2 $\mu$g, Primer P570SAL 2 $\mu$g
Tube C: Primer P897T2 2 $\mu$g, Primer P430SAL 2 $\mu$g
Tube D: Primer P897T2 2 $\mu$g, Primer P290SAL 2 $\mu$g
Tube E: Primer P150T2 2 $\mu$g, Primer P897SAL 2 $\mu$g
Tube F: Primer P257T2 2 $\mu$g, Primer P897SAL 2 $\mu$g
Tube G: Primer P365T2 2 $\mu$g, Primer P897SAL 2 $\mu$g
Tube H: Primer P518T2 2 $\mu$g, Primer P897SAL 2 $\mu$g To each of the tubes were added 50ng of the plasmid ptrp-UB-KHCV897 comprising KHCV 897 DNA(ATCC 68640), 10 $\mu$l of 10x polymerase buffer solution, 10 $\mu$l of 2 mM dNTP(2 mM dGTP, 2 mM dATP, 2 mM TTP, 2 mM dCTP), 2.5 unit of Taq polymerase; and distilled water was added thereto to adjust the total volume to be 100 $\mu$l.

50 $\mu$l of mineral oil was added to each of the reaction mixtures to prevent evaporation; and PCRs were carried out by repeating 25 times the same thermal cycles as in Reference Example 6.

(1-3) Separation and purification of PCR products

The PCR products obtained in the above (1-2) were subjected to 5% polyacrylamide gel electrophoresis. As a result, it was confirmed that about 650 bp of DNA in tube A, about 580 bp of DNA in tube B, about 440 bp of DNA in tube C, about 300 bp of DNA in tube D, about 160 bp of DNA in tube E, about 260 bp of DNA in tube F, about 370 bp of DNA in tube G, about 520 bp of DNA in tube H were amplified, respectively. The DNAs were purified by the same polyacrylamide gel electrophoresis as above and named segment 652, segment 570, segment 430, segment 290, segment 150, segment 257, segment 365, and segment 518, respectively. The position of each fragment in KHCV 897 DNA and primers used for the preparation thereof are shown in FIG. 4.

<Step 2> Preparation of expression vector (2-1) Digestion of the segments and vector DNA with restriction endonucleases 2 $\mu$g of each of DNA segments obtained in the <Step 1> was completely digested with SacII and SalI in NEB buffer solution 3 referred to in Reference Example 1. The resulting fragments were named fragments 652-T2/L, 570-T2/L, 430-T2/L, 290-T2/L, 150-T2/L, 257-T2/L, 365-T2/L, and 518-T2/L, respectively.

On the other hand, 2 $\mu$g of plasmid ptrpH-UB-CORE14 (ATCC 68642; see Korean Patent Laid-open Publication No. 93-683) was also completely digested with SacII and-SalI in NEB buffer solution 3. The resulting mixture was subjected to 7% agarose gel electrophoresis to isolate 2.7 kb fragment, which was named fragment ptrpH-UB-T2/L.

The above fragments were used in the ligation reactions as follows:

Ligation tube A was provided with 100 ng of fragment 652-T2/L;

ligation tube B was provided with 100 ng of fragment 570-T2/L;

ligation tube C was provided with 100 ng of fragment 430-T2/L;

ligation tube D was provided with 100 ng of fragment 290-T2/L;

ligation tube E was provided with 100 ng of fragment 150-T2/L;

ligation tube F was provided with 100 ng of fragment 257-T2/L;

ligation tube G was provided with 100 ng of fragment 365-T2/L;

and ligation tube H was provided with 100 ng of fragment 518-T2/L.

To each of the tubes were added 50 ng of fragment ptrpH-UB-T2/L, 2 $\mu$l of 10 x ligation buffer solution, 10 units of T4 DNA ligase; and distilled water was added to adjust the total volume to be 20 $\mu$l. The ligation was carried out at 16° C. for 12 hours.

*E. coli* HB101(ATCC 33694) cell aliquots were transformed with each of the ligation mixture, respectively; and desired recombinant expression vectors were isolated therefrom, in accordance with Reference Example 4.

The vector containing fragment 652 was isolated and named ptrpH-UB-KHCV 652; the vector containing fragment 570 was isolated and named ptrpH-UB-KHCV 570; the vector containing fragment 430 was isolated and named ptrpH-UB-KHCV 430; the vector containing fragment 290 was isolated and named ptrpH-UB-KHCV 290; the vector containing fragment 150 was isolated and named ptrpH-UB-KHCV 150; the vector containing fragment 257 was isolated and named ptrpH-UB-KHCV 257; the vector containing fragment 365 was isolated and named ptrpH-UB-KHCV 365; and the vector containing fragment 518 was isolated and named ptrpH-UB-KHCV 518(see FIG. 5).

<Step 3> Expression of KHCV 897 DNA partial fragments

*E. coli* W3110(ATCC 37339) was transformed with each of the vectors prepared in the above <Step 2>.

Transformed *E. coli* cells were cultured with shaking in liquid Luria medium(6% Bacto-tryptone, 0.5% yeast extract, 1% NaCl) containing 50 $\mu$g/ml of ampicillin at 37° C. for 12 hours. 3 ml of the culture was transferred into 300 ml of M9 medium (40 mM $K_2HPO_4$, 22 mM $KH_2PO_4$, 8.5 mM NaCl, 18.7 mM $NH_4Cl$, 1% glucose, 0.1 mM $MgSO_4$, 0.1 mM $CaCl_2$, 0.4% casamino acid, 10 $\mu$g/ml Vit. $B_1$, 40 $\mu$g/ml ampicillin); and cultured with shaking for 4 hours at 37° C. When its O.D. value at 650 nm reached 0.3, indole acrylic acid(IAA) was added to the culture to adjust the final concentration to be 50 $\mu$g/ml. After 5 hours, the resulting culture was centrifuged at 11,000 rpm for 25 min. to collect the *E. coli* cell precipitates.

<Step 4> Identification of epitopes of KHCV 897 protein

Each of the cell precipitates obtained in the above <Step 3> was subjected to 15% SDS-PAGE by employing Laemmli's method (Nature 227, 680(1970)); and the gel was stained with Coomassie brilliant blue R250 to confirm the expression of the recombinant proteins. The result is shown in FIG. 6A.

In FIG. 6A, lane M represents the standard molecular size marker, lane 1 shows the products of *E. coli* having plasmid without any KHCV DNA fragment; lane 2 shows the products of *E. coli* transformed with ptrpH-UB-KHCV 897; lane 3 shows the products of *E. coli* transformed with ptrpH-UB-KHCV 290; lane 4 shows the products of *E. coli* transformed with ptrpH-UB-KHCV 430; lane 5 shows the products of *E. coli* transformed with ptrpH-UB-KHCV 570; lane 6 shows the products of *E. coli* transformed with ptrpH-UB-KHCV 652; lane 7 shows the products of *E. coli* transformed with ptrpH-UB-KHCV 518; lane 8 shows the products of *E. coli* transformed with ptrpH-UB-KHCV 365; lane 9 shows the products of *E. coli* transformed with ptrpH-UB-KHCV 257;

and lane 10 shows the products of E. coli transformed with ptrpH-UB-KHCV 150.

The proteins separated on the gel were blotted onto a nitrocellulose filter(Bio-Rad Lab., pore size 0.22 µm, California, U.S.A.) by employing Towbin's method (Towbin, et al., Proc. Natl. Acad. Sci. U.S.A. 76, 4750 (1979)). The filter was put in PBS(10 mM phosphate, pH 7.0, 0.15M NaCl) containing 0.5% Tween 20; and shaken gently at room temperature for 2 hours to block the non-specific binding of IgG to the proteins. The filter was put in IgG solution prepared by diluting IgG purified from Korean HCV patients with PBS containing 0.5% gelatin and 0.05% Tween 20 to adjust the final concentration to be 16 µg/ml; and mildly shaken for 1 hour at room temperature to react the protein and IgG. The filter was then washed 4 times with PBS containing 0.2% Tween 20, each for 5 minutes. The filter was put in an anti-human IgG antibody solution prepared by diluting goat anti-human IgG labeled with horseradish peroxidase (goat anti-human IgG-HRP, Bio-Rad Lab., California, U.S.A.) with 500-fold volume of PBS containing 0.5% gelatin and 0.05% Tween 20; and shaken at room temperature for 1 hour The filter was washed 4 times with PBS containing 0.2% Tween 20, each for 5 minutes; and then, twice with 50 mM Tris buffer solution(pH 7.0). To the filter were added 50 mM Tris buffer solution containing 400 µg/ml 4-chloro-1-naphthol and 0.03% hydrogen peroxide to develop a color reaction. The results from the above western blotting are shown in FIG. 6B. In FIG. 6B, lane M and lanes 1 to 10 represent the same samples as FIG. 6A; and lanes 5 to 10 show positive results, while lanes 3 and 4 show negative results.

Figure 6A:
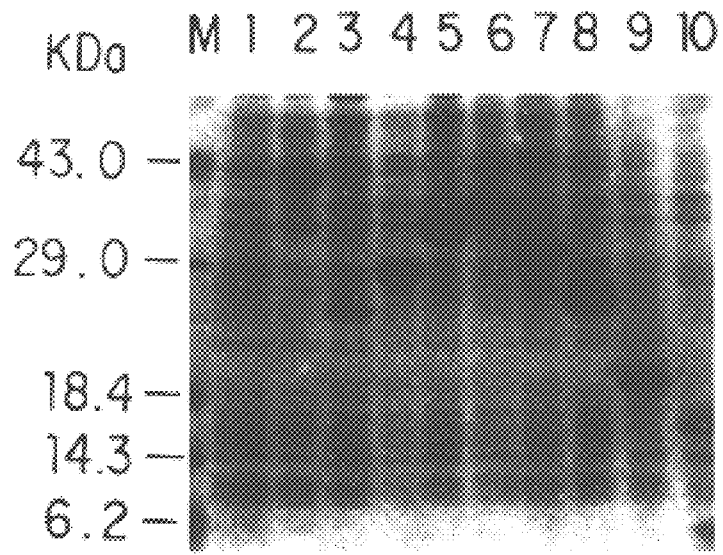
FIG. 6A represents the result of SDS polyacrylamide gel electrophoresis(SDS-PAGE) after the expression of a KHCV897 DNA fragment in *E. coli* cells.
Figure 6B:
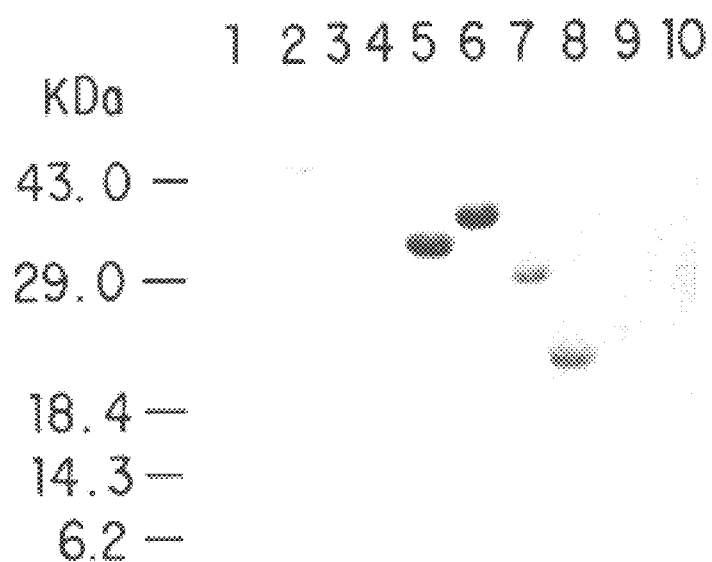
FIG. 6B shows the result of western blotting analysis with the gel of FIG. 6A by using a serum taken from a hepatitis C patient.

Therefore, as can be seen from FIGS. 6A and 6B, the epitope of KHCV 897 protein exists in carboxyl terminal region of KHCV 897 protein(KHCV 365 protein), i.e., it is encoded by 366 base pairs consisting of the 4348th to the 4713rd nucleotides of KHCV-LBC1. However, said KHCV 365 protein exhibits lower immunoreactivity than KHCV 897 protein. From this fact, it can be presumed that amino acids in the N-terminal of KHCV 365 protein cannot serve as epitope when they are expressed as N-terminal amino acids. Therefore, KHCV 518 protein which comprise said KHCV 365 protein and extencted N-terminal amino acids and has immunoreactivity similar to that of KHCV 897 protein were used hereinafter for preparing HCV diagnostic agents.

Example 2

Determination of Epitopes of HCV Envelope Protein

<Step 1> Amplification of the partial fragments of HCV envelope gene (1–1) Preparation of primers In order to amplify KHCV envelope gene fragments and to clone each into an expression vector comprising ubiquitin gene under the control of trp promotor, the following primers were synthesized:

Primer PE1T2 (SEQ ID NO: 11): 5'-TGAGACTCCGCG GTGGTTATGAAGTGGGCAACGCGTCC-3' comprising a recognition site of SacII and the 916th to the 937th nucleotides of KHCV-LBC1;

Primer PE1DT2 (SEQ ID NO: 12): 5'-TGAGACTCCGCG GTGGTGACTTGCTCGTTGGGGTAGCT-3' comprising a recognition site of SacII and the 1129th to the 1149th nucleotides of KHCV-LBC1;

Primer PE1EGT2 (SEQ ID NO: 13): 5'-TGAGACTCCGCG GTGGTGTTTCCCAGCTGTTCACCTTC-3' comprising a recognition site of SacII and the 1201st to the 1221st nucleotides of KHCV-LBC1;

Primer PE1FT2 (SEQ ID NO: 14): 5'-TGAGACTCCG CGGTGGTACAACAGCCCTAGTGGTATCG-3' comprising a recognition site of SacII and the 1327th to the 1347th nucleotides of KHCV-LBC1;

Primer PE1AXHO (SEQ ID NO: 15): 5'-AAAAAACTCGA GTTAGACATGGCGTCGCAATGTCGT-3' comprising a stop codon to terminate translation after the 1128th nucleotide of KHCV-LBC1, and a recognition site of XhoI;

Primer PE1BXHO (SEQ ID NO: 16): 5'-AAAAAACTCGA GTTAAAGGAAAACAGATCCGCAGAG-3' comprising a stop codon to terminate translation after the 1200th nucleotide of KHCV-LBC1, and a recognition site of XhoI;

Primer PE1CDEXHO (SEQ ID NO: 17): 5'-AAAAAACTC GAGTTAAGGCGACCAGT-CATCATCAT-3' comprising a stop codon to terminate translation after the 1326th nucleotide of KHCV-LBC1, and a recognition site of XhoI;

Primer PE1XHO (SEQ ID NO: 18): 5'-AAAAAACTCGA GTTACCCTGTCACGTGGGTGGTTCC-3' comprising a stop codon to terminate translation after the 2835th nucleotide of KHCV-LBC1, and a recognition site of XhoI;

Primer PE2T2 (SEQ ID NO: 19): 5'-TGAGACTCCGC GGTGGTGGGGCGCAAGGTCGGGCCGCT-3' comprising a recognition site of SacII and the 1509th to the 1529th nucleotides of KHCV-LBC1;

Primer PE2BT2 (SEQ ID NO: 20): 5'-TGAGACTCCG CGGTGGTGGTCCCATCACTTACACTGAG-3' comprising a recognition site of SacII and the 1749th to the 1769th nucleotides of KHCV-LBC1;

Primer PE2DFT2 (SEQ ID NO: 21): 5'-TGAGACTCCG CGGTGGTGGCACTGGGTTCACCAAGACA-3' comprising a recognition site of SacII and the 2010th to the 2030th nucleotides of KHCV-LBC1;

Primer PE2ET2 (SEQ ID NO: 22): 5'-TGAGACTCCGCGG TGGTACTCGGGGAGAGCGTTGTGAC-3' comprising a recognition site of SacII and the 2280th to the 2300th nucleotides of KHCV-LBC1;

Primer PE2AXHO (SEQ ID NO: 23): 5'-AAAAAACTCGA GTTACCACCCCTGCGCGAATGTATC-3' comprising a stop codon to terminate translation after the 1748th nucleotide of KHCV-LBC1, and a recognition site of XhoI;

Primer PE2BCXHO (SEQ ID NO: 24): 5'-AAAAAACTCG AGTTAATTCATCCAGGTACAACCGAA-3' comprising a stop codon to terminate translation after the 2009th nucleotide of KHCV-LBC1, and a recognition site of XhoI;

Primer PE2DXHO (SEQ ID NO: 25): 5'-AAAAAACTCG AGTTACCAGTTGCATGCGGCGTCGAG-3' comprising a stop codon to terminate translation after the 2279th nucleotide of KHCV-LBC1, and a recognition site of XhoI; and Primer PE2XHO (SEQ ID NO: 26): 5'-AAAAAACTCG AGTTACGCGTCCGCCAGAAGAAGGAAGAG-3' comprising a stop codon to terminate translation after the 2528th nucleotide of KHCV-LBC1, and a recognition site of XhoI.

(1-2) Polymerase chain reaction 14 different test tubes were prepared, which were provided with the primers as follows:

Tube A: Primer PE1T2 2 µg, Primer PE1XHO 2 µg
Tube B: Primer PE1T2 2 µg, Primer PE1AXHO 2 µg
Tube C: Primer PE1T2 2 µg, Primer PE1BXHO 2 µg
Tube D: Primer PE1T2 2 µg, Primer PE1CDEXHO 2 µg
Tube E: Primer PE1DT2 2 µg, Primer PE1CDEXHO 2 µg
Tube F: Primer PE1EGT2 2 µg, Primer PE1CDEXHO 2 µg Tube G: Primer PE1FT2 2 μg, Primer PE1XHO 2 μg
Tube H: Primer PE1EGT2 2 μg, Primer PE1XHO 2 μg
Tube I: Primer PE2T2 2 μg, Primer PE2AXHO 2 μg
Tube J: Primer PE2BT2 2 μg, Primer PE2BCXHO 2 μg
Tube K: Primer PE2T2 2 μg, Primer PE2BCXHO 2 μg
Tube L: Primer PE2DFT2 2 μg, Primer PE2DXHO 2 μg
Tube M: Primer PE2ET2 2 μg, Primer PE2XHO 2 μg
Tube N: Primer PE2DFT2 2 μg, Primer PE2XHO 2 μg To each of the tubes were added each 50 ng of the vector ptrpH-UB-El comprising envelope 1 gene(ATCC 68878) for tubes A to H and the vector pYLBC-A/G-UB-E2N and pYLBC-A/G-UB-E2C comprising envelope 2 gene(ATCC 69886 and 74117) for tubes I to N as a template, 10 μl of 10x polymerase buffer solution, 10 μl of 2 mM dNTP(2 m dGTP, 2 m dATP, 2 mM TTP, 2 mM dCTP), 2.5 μl of 10 unit Taq polymerase; and distilled water was added thereto to adjust the total volume to be 100 μl.

To each of the reaction mixtures was added 50 μl of mineral oil to prevent evaporation; and PCRs were carried out by repeating 25 times the same thermal cycles as in Reference Example 6.

(1-3) Separation and purification of PCR products

Figure 7:
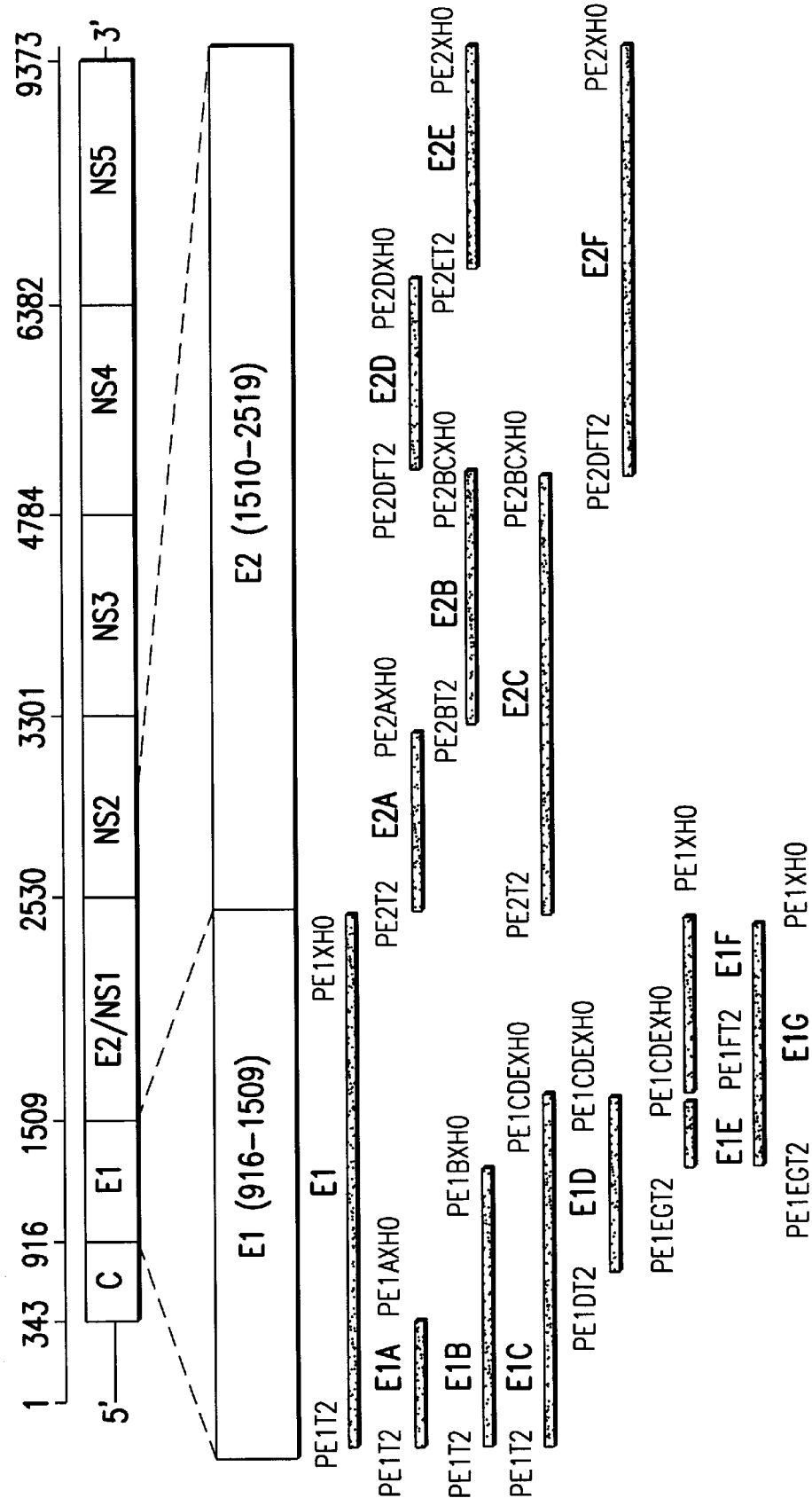
FIG. 7 represents the position of each of the primers used for amplifying various DNA fragments of a gene encoding an envelope protein by PCR.

The PCR products obtained in the above (1-2) were subjected to 5% polyacrylamide gel electrophoresis. As a result, it was confirmed that about 600 bp of DNA in tube A, about 220 bp of DNA in tube B, about 300 bp of DNA in tube C, about 410 bp of DNA in tube D, about 200 bp of DNA in tube E, about 110 bp of DNA in tube F, about 190 bp of DNA in tube G, about 300 bp of DNA in tube H, about 210 bp of DNA in tube I, about 300 bp of DNA in tube J, about 505 bp of DNA in tube K, about 290 bp of DNA in tube L, about 240 bp of DNA in tube M, and about 520 bp of DNA in tube N were amplified, respectively. The DNAs were purified by the same polyacrylamide gel electrophoresis as above and named segment E1, segment E1A, segment E1B, segment E1C, segment E1D, segment E1E, segment E1F, segment E1G, segment E2A, segment E2B, segment E2C, segment E2D, segment E2E, and segment E2F. The positions of each segments of the envelope gene and primers used for the preparation thereof are shown in FIG. 7.

<Step 2> Preparation of expression vector

2 μg of each of DNA segments obtained in the (1-3) of <Step 1> was completely digested with SacII and XhoI in NEB buffer solution 3 referred to in Reference Example 1.

Each of 14 ligation tubes was provided with 100 ng of DNA segments obtained above. To each of the tubes were added 50ng of fragment ptrpH-UB-T2/L which was obtained in the <Step 2> of Example 1, 2 μl of 10x ligation buffer solution, 10 units of T4 DNA ligase; and distilled water was added to adjust the total volume to be 20 μl. The ligation was carried out at 16° C. for 12 hours.

Fourteen E. coli W3110(ATCC 37339) cell aliquots were transformed with each of the ligation mixtures, respectively.

The vector containing segment E1 was isolated and named ptrpH-UB-E1; the vector containing segment E1A was isolated and named ptrpH-UB-E1A; the vector containing segment E1B was isolated and named ptrpH-UB-E1B; the vector containing segment E1C was isolated and named ptrpH-UB-E1C; the vector containing segment E1D was isolated and named ptrpH-UB-E1D; the vector containing segment E1E was isolated and named ptrpH-UB-E1E; the vector containing segment E1F was isolated and named ptrpH-UB-E1F; the vector containing segment E1G was isolated and named ptrpH-UB-E1G; the vector containing segment E2A was isolated and named ptrpH-UB-E2A; the vector containing segment E2B was isolated and named ptrpH-UB-E2B; the vector containing segment E2C was isolated and named ptrpH-UB-E2C; the vector containing segment E2D was isolated and named ptrpH-UB-E2D; the vector containing segment E2E was isolated and named ptrpH-UB-E2E; and the vector containing segment E2F was isolated and named ptrpH-UB-E2F(see FIG. 8).

<Step 3> Expression of envelope gene segments

E. coli W3110(ATCC 37339) cells transformed with each of the plasmids containing envelope gene fragments prepared in the above <Step 2> were cultured in the same manner as in <Step 3> of Example 1; and then centrifuged to collect the E. coli cell precipitates.

<Step 4> Identification of epitopes of envelope protein

Figure 9A:
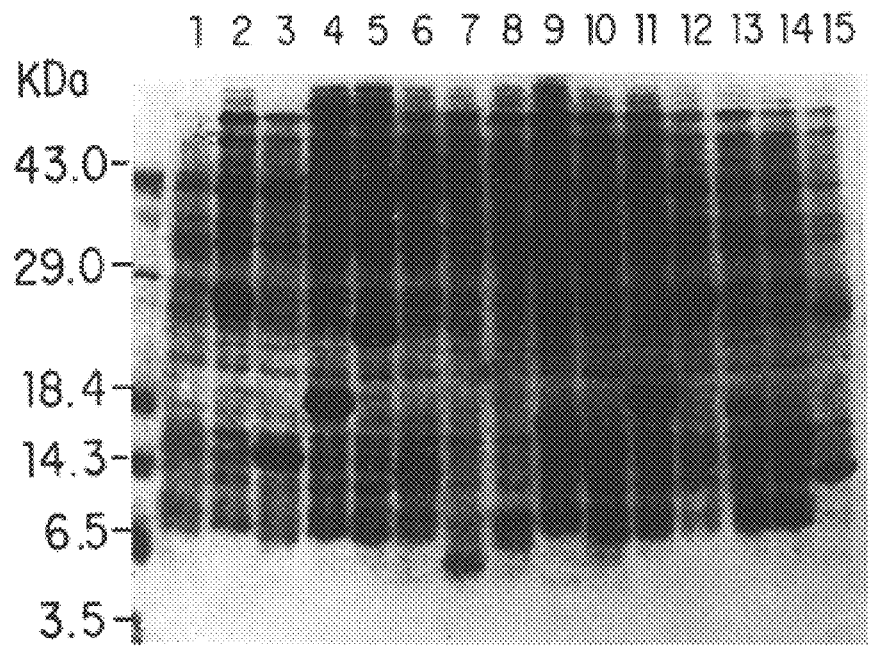
FIG. 9A shows the result of SDS polyacrylamide gel electrophoresis(SDS-PAGE) after the expression of various DNA fragments encoding a portion of an envelope protein in *E. coli* cells.
Figure 9B:
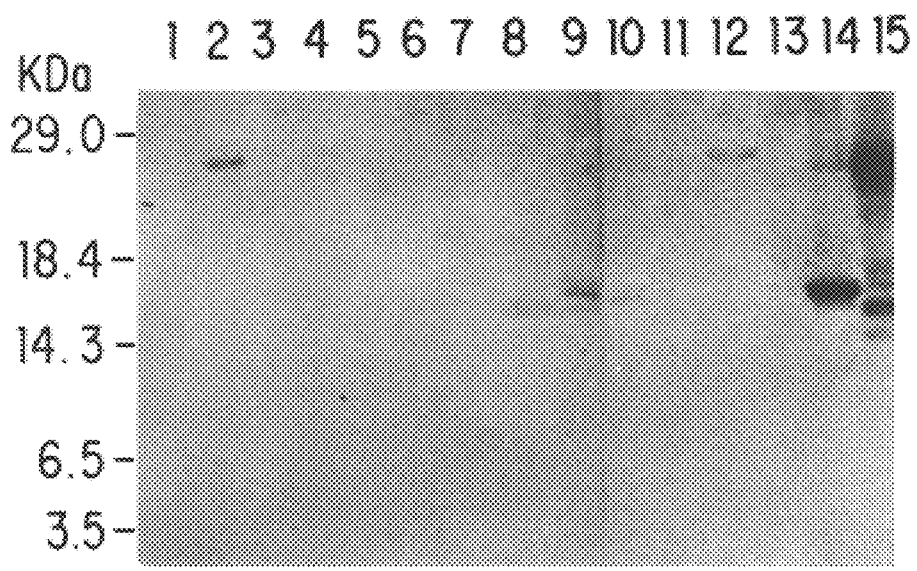
FIG. 9B shows the result of western blotting analysis with the gel of FIG. 9A by using a serum taken from a hepatitis C patient.

Epitopes of envelope protein were identified by employing the cell precipitates of <Step 3> in the same manner as in <Step 4> of Example 1; and the result is shown in FIG. 9, wherein A is the result of SDS-PAGE and B is the result of western blotting.

In FIG. 9, lane 1 shows the products of E. coli having plasmid without any envelope gene segment; lane 2 shows the products of E. coli transformed with ptrpH-UB-E1; lane 3 shows the products of E. coli transformed with ptrpH-UB-E1A; lane 4 shows the products of E. coli transformed with ptrpH-UB-E1B; lane 5 shows the products of E. coli transformed with ptrpH-UB-E1C; lane 6 shows the products of E. coli transformed with ptrpH-UB-E1D; lane 7 shows the products of E. coli transformed with ptrpH-UB-E1E; lane 8 shows the products of E. coli transformed with ptrpH-UB-E1F; lane 9 shows the products of E. coli transformed with ptrpH-UB-E1G; lane 10 shows the products of E. coli transformed with ptrpH-UB-E2A; lane 11 shows the products of E. coli transformed with ptrpH-UB-E2B; lane 12 shows the products of E. coli transformed with ptrpH-UB-E2C; lane 13 shows the products of E. coli transformed with ptrpH-UB-E2D; lane 14 shows the products of E. coli transformed with ptrpH-UB-E2E; and lane 15 shows the products of E. coli transformed with ptrpH-UB-E2F.

The result of western blotting analysis employing the E. coli cells transformed with a plasmid comprising various envelope gene segments to confirm the specificity thereof against the anti-KHCV antibodies obtained from the serum of Korean hepatitis C patient is shown in Table I below, as well as in FIG. 9B.

TABLE I

Result of Western Blotting analysis employing KHCV envelope protein fragments

| Lane | protein fragment | position (No. of a.a.) | | Western blotting signal |
|---|---|---|---|---|
| 2 | UBE1 | E1 | 1–198 | + |
| 3 | UBE1A | E1 | 1–72 | − |
| 4 | UBE1B | E1 | 1–99 | − |
| 5 | UBE1C | E1 | 1–136 | (+) |
| 6 | UBE1D | E1 | 72–136 | (+) |
| 7 | UBE1E | E1 | 100–136 | ((+)) |
| 8 | UBE1F | E1 | 136–198 | + |
| 9 | UBE1G | E1 | 100–198 | + |
| 10 | UBE2A | E2 | 1–67 | (+) |
| 11 | UBE2B | E2 | 68–167 | − |
| 12 | UBE2C | E2 | 1–167 | (+) |
| 13 | UBE2D | E2 | 168–262 | − |
| 14 | UBE2E | E2 | 263–340 | + |
| 15 | UBE2F | E2 | 168–340 | + |

*Western signal
+: positive
(+) weak
((+)) very weak
−: negative

As can be seen from Table I and FIG. 9B, the lanes 9, 10 and 14 which represent the products of *E. coli* transformed with a plasmid comprising envelope gene segments E1G, E2A and E2E, respectively, show positive signals, while the other lanes which represent the products of E. coli transformed with a plasmid comprising envelope gene segments E1A, E1B, E2B, E2D, etc. show negative signals.

Therefore, it has been found that epitopes of envelope protein exist in the carboxyl terminal region of KHCV envelope 1 protein which was expressed from the 309 base pairs corresponding to 1201st to 1509th nucleotides of KHCV-LBC1(E1G protein); in the amino terminal region of KHCV envelope 2 protein which was expressed from the 240 base pairs corresponding to 1510th to 1749th nucleotides of KHCV-LBC1(E2A protein); and in the carboxyl terminal region of KHCV envelope 2 protein which was expressed from the 249 base pairs corresponding to 2281st to 2529th nucleotides of KHCV-LBC1 (E2E protein)(see FIGS. 2A–B for the amino acid and nucleotide sequences of E1G, E2A and E2E protein).

The following Examples 3 to 5 show the preparation of recombinant proteins comprising more than one epitope of HCV.

Example 3

Preparation of KHCV UB CORE518 Protein
<Step 1> Amplification of KHCV 518 DNA
(1-1) Preparation of primers In order to amplify KHCV 518 DNA(which consists of the region from the 4196th to the 4713rd nucleotides of KHCV-LBC1) and to clone it into an expression vector comprising ubiquitin gene and KHCV CORE14 DNA (ATCC 68642; see Korean Patent Publication No. 93-683) under the control of trp promotor, the following primers were synthesized.
Primer PK518T2 (SEQ ID NO: 27): 5'-TGAGACTCCG CGGTGGTGGAGGAGGAGGAGGAGGAAT-CACCACAG GCGCCCCTATC-3' comprising a recognition site of SacII, 6 glycine codons, and the 4195th to the 4215th nucleotides of KHCV-LBC1; and
Primer PK518SAL (SEQ ID NO: 28): 5'-AAAAAAGTCG ACTATTAACACGTATTACAGTCGATCAC-3' comprising a stop codon to terminate translation after the 4713rd nucleotide of KHCV-LBC1, and a recognition site of SalI.
(1-2) Polymerase chain reaction A test tube was provided with the primer PK518T2 2 μg and primer PK518SAL 2 μg. To the tube were added 50 ng of KHCV-LBC1 DNA(ATCC 75008), 10 μl of 10x polymerase buffer solution, 10 μl of 2 mM dNTP(2 mM dGTP, 2 mM dATP, 2 mM TTP, 2 mM dCTP), 2.5 unit of Taq polymerase; and distilled water was added thereto to adjust the total volume to be 100 μl.

To the reaction mixture was added 50 μl of mineral oil to prevent evaporation; and PCR was carried out by repeating 25 times the same thermal cycles as in Reference Example 6.
(1-3) Separation and purification of PCR product The PCR product obtained in the above (1-2) was subjected to 5% polyacrylamide gel electrophoresis. As a result, it was confirmed that about 520 bp of DNA was amplified. The DNA was purified by the same polyacrylamide gel electrophoresis as (1-2) above and named fragment GLYK518.
<Step 2> Preparation of expression vector 2 μg of plasmid ptrpH-UB-CORE14(ATCC 68642; see Korean Patent Laid-open Publication No. 93-683) was completely digested with SalI in NEB buffer solution 3 referred to in Reference Example 1, and then partially digested with SacII under the same condition The resulting mixture was subjected to 7% agarose gel electrophoresis to isolate 3.0 kb fragment, which was named fragment ptrpH-UB-CORE (T2)/L.

2 μg of the fragment GLYK518 obtained in the (1-3) of <Step 1> was completely digested with SacII and SalI in NEB buffer solution 3 referred-to in Reference Example 1.

Figure 10:
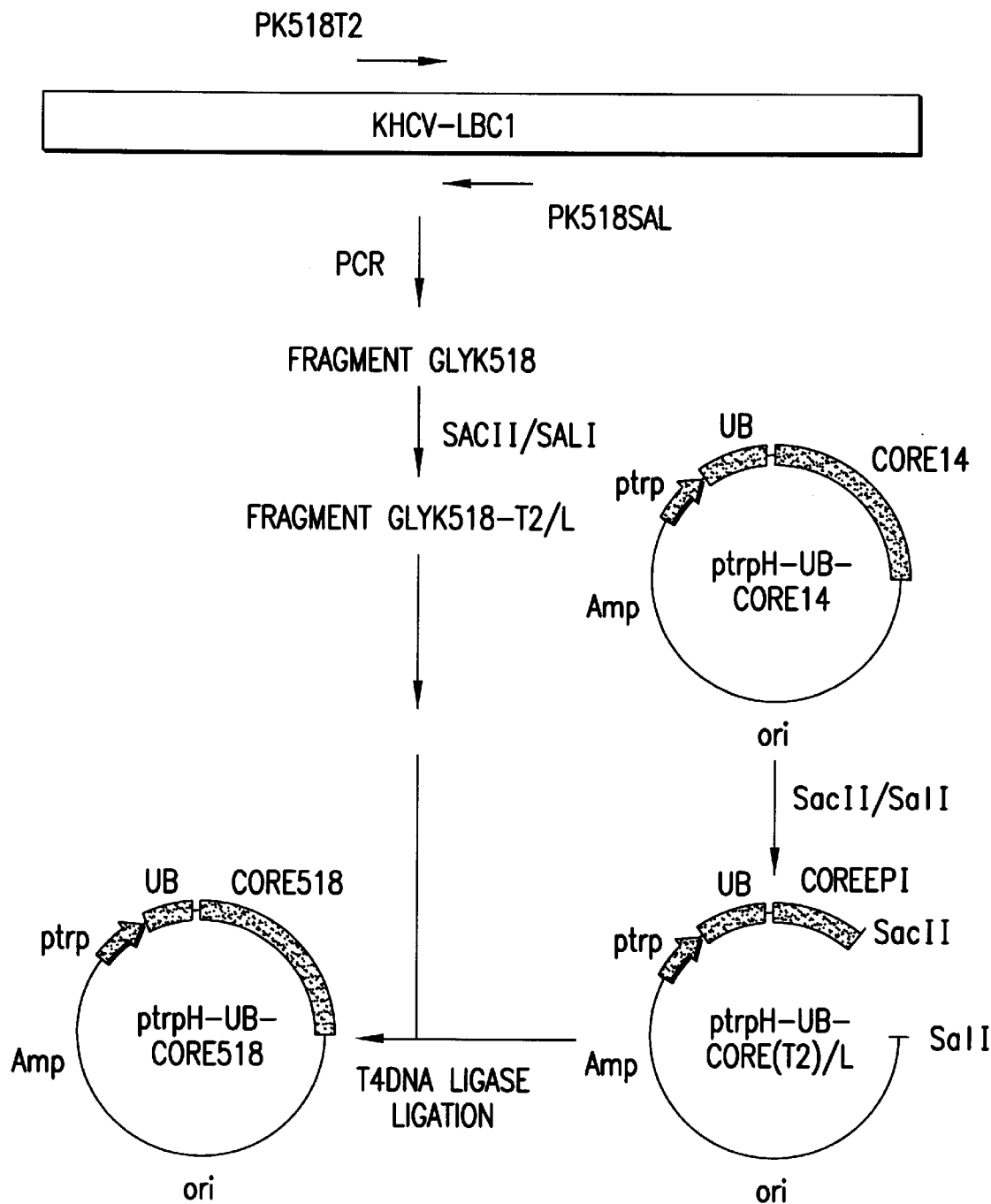
FIG. 10 delineates a schematic diagram for preparing an expression vector constructed for the purpose of expressing UBCORE518 protein.

A reaction tube was provided with 10 ng of DNA fragment obtained above To the tube were added 50 ng of the fragment ptrpH-UB-CORE(T2)/L, 2 μl of 10x ligation buffer solution, 10 units of T4 DNA ligase; and distilled water was added to adjust the total volume to be 20 μl. The ligation was carried out at 16° C. for 12 hours E. coli W3110(ATCC 37339) was transformed with the ligation mixture to obtain recombinant E. coli transformant containing plasmid ptrpH-UB-CORE518 comprising the fragment GLYK518(see FIG. 10) connected with ubiquitin gene and KHCV CORE 14 DNA in an open reading frame ("CORE 518 DNA").
<Step 3> Expression of CORE518 DNA E. coli W3110 cells transformed with the plasmid ptrpH-UB-CORE518 prepared in the above <Step 2> were cultured in the same manner as in <Step 3> of Example 1; and then centrifuged to collect the E. coli cell precipitates.

Figure 11A:
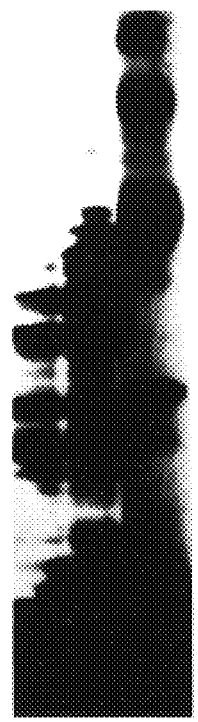
FIG. 11A shows the result of SDS polyacrylamide gel electrophoresis(SDS-PAGE) after the expression of UBCORE518 DNA fragment in *E. coli* cells.
Figure 11B:
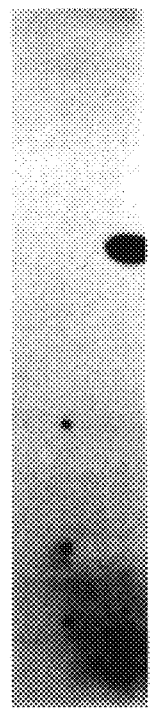
FIG. 11B shows the result of western blotting analysis with the gel of FIG. 11A by using a serum taken from a hepatitis C patient.
Figure 12:
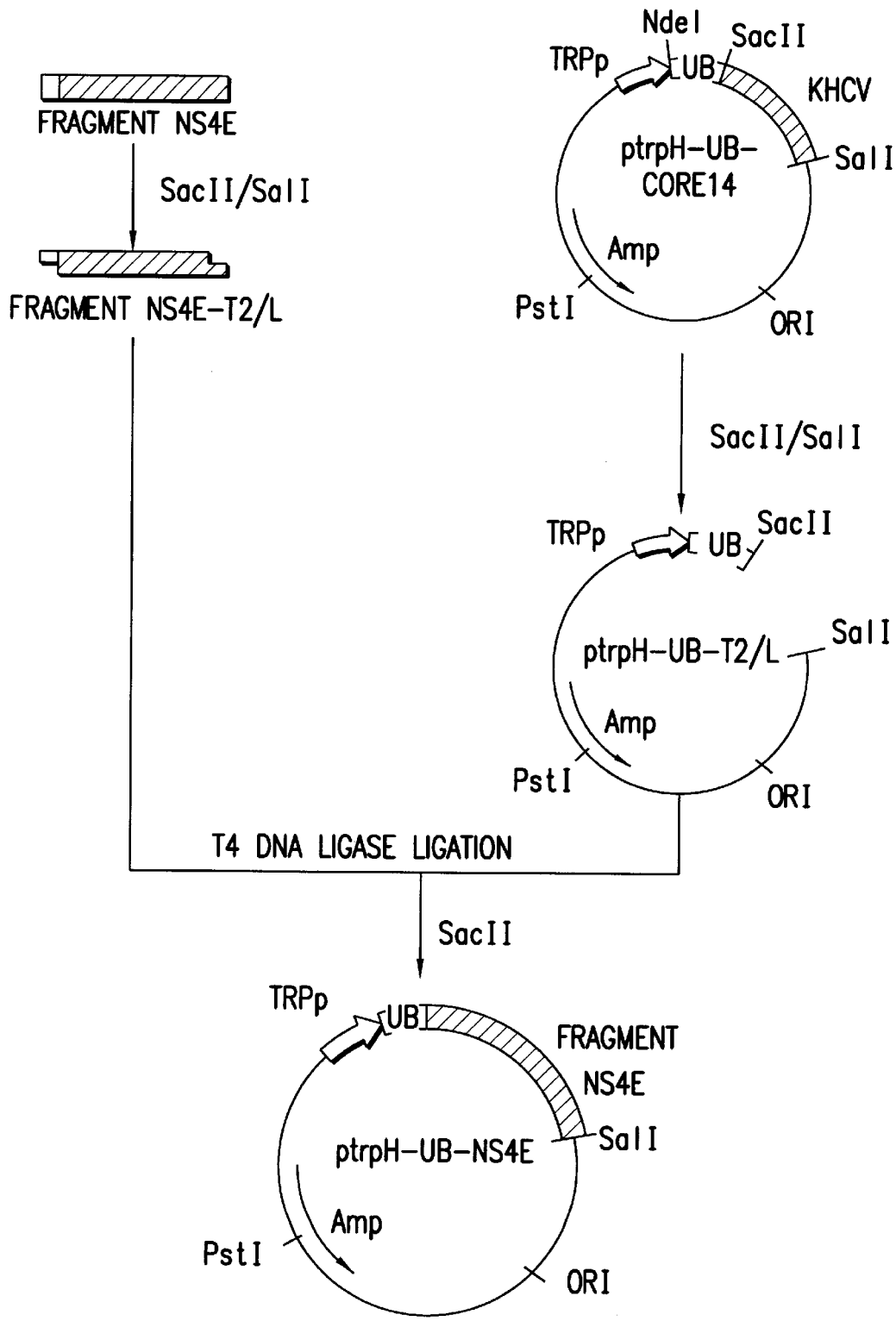
FIG. 12 shows a schematic diagram for preparing an expression vector constructed for the purpose of expressing a recombinant DNA comprising a ubiquitin gene and the DNA fragment encoding an epitope of non-structural protein 4(NS4E protein)

The reactivity of the expressed CORE518 protein with a serum taken from a hepatitis C patient was confirmed by employing the above cell precipitates in the same manner as in <Step 4> of Example 1; and the result is shown in FIG. 11, wherein A is the result of SDS-PAGE and B is the result of Western blotting.

In FIG. 11, lanes 1 and 4 show the products of E. coli not having plasmid ptrpH-UB-CORE518; lanes 2 and 5 show the products of E. coli transformed with ptrpH-UB-CORE518; and lane 3 shows the standard molecular size markers, i.e., 70, 43, 29, 18 and 14 kilodaltons from the top of the gel.
<Step 4> Purification of UBCORE518 protein
(4-1) Cell disruption and removal of soluble proteins b 3g of E. coli cell precipitate obtained in <Step 3> was suspended in 40 ml of buffer 1(20 mM Tris, pH 8.0, 1 mM EDTA, 10 mM β-mercaptoethanol, 1 mM phenyl methyl sulfonyl fluoride, 1 μg/ml pepstatin A). Lysozyme was added to the suspension to adjust the final concentration to be 0.2mg/m2, and the resulting solution was incubated on ice for 30 minutes. The resultant was subjected to ultrasonication in an ice bath for 15 minutes with an ultrasonicater (HEAT SYSTEMS ULTRASONICS INC., W225, U.S.A.) at an output of 80% and 50% duty-cycle to disrupt the cell and obtain a homogenate of E. coli cells.

The cell homogenate obtained in the above was centrifuged at 15,000 rpm for 25 minutes with a centrifuge (Beckman J2-21, Rotor JA 20) to remove dissolved proteins and obtain insoluble precipitate.
(4-2) Washing of insoluble precipitate The precipitate obtained in (4-1) was suspended in 4 m. of buffer 2(20 mM Tris, pH 8.0, 1 mM EDTA, 10 mM β-mercaptoethanol) containing 1% Triton X-100. The suspension was stirred at room temperature for 30 minutes and centrifuged at 15,000 rpm for 25 minutes with a centrifuge (Beckman J2-21, Rotor JA 20) to remove dissolved proteins and obtain insoluble precipitate.
(4-3) Dissolution of insoluble precipitate The insoluble precipitate of (4-2) was suspended in 100 ml of buffer 3(50 mM Tris, pH 9.0, 1 mM EDTA, 10 mM β-mercapto-ethanol) containing 4M urea. The suspension was stirred at room temperature for 2 hours and centrifuged to remove insoluble precipitate and obtain the supernatant.

(4-4) DEAE-Sepharose ion exchange chromatography

The supernatant obtained in (4-3) was passed through DEAE-Sepharose column(Pharmacia, 1.25 cm×4 cm) equilibrated with the above buffer 3 at a flow rate of 4 ml/min.; and same buffer was added to elute free proteins remains in column. Then, 200 ml of buffer 3 having a concentration gradient of 0 to 0.3M NaCl was added at a flow rate of 4 ml/min. to elute the bound proteins and collect the eluate by 2 ml fractions. The protein fractions were subjected to 15% SDS-PAGE to collect the fractions comprising UBCORE518 protein.

(4-5) FPLC-MONO S chromatography

The protein fractions comprising UBCORE518 protein collected in (4-4) were concentrated to a volume of 20 ml with YM10 ultrafiltration membrane (Amicon, U.S.A.). The concentrate was passed over G-25 column(Pharmacia, 2.5 cm×90 cm) equilibrated with the buffer 4(50 mM phosphate, pH 6.0, 1 mM EDTA, 10 mM B-mercaptoethanol) containing 4M urea. The eluate was in turn passed over FPLC-Mono S column(Pharmacia, HR 5/5, 0.5 cm×5 cm) equilibrated with the same buffer at a flow rate of 0.7 ml/min.; and same buffer was added to elute free proteins remained in column. Then, same buffer containing 0.2M of NaCl was added to elute the bound proteins. 200 ml of buffer 5(10 mM phosphate, pH 7.0) having a linear concentration gradient of 0.2 to 0.4M NaCl was added to elute the bound proteins and collect the eluate by 0.7 ml fractions. The protein fractions were subjected to 15% SDS-PAGE to collect the fractions comprising UBCORE518 protein having a purity of at least 95%; and the antigenic specificity of the purified protein was confirmed by employing western blotting analysis.

Example 4

Preparation of KHCV UB NS4E1E2 Protein

<Step 1> Expression vector for KHCV NS4E DNA (1-1) Preparation of primers

In order to prepare KHCV NS4E DNA(which consists of the region from the 5422nd to the 5547th nucleotides of KHCV-LBC1) and to clone it into an expression vector comprising ubiquitin gene under the control of trp, promotor, the following primers were synthesized:

Primer PNS4ET2 (SEQ ID NO: 29): 5'-TGAGACTCC GCGGTGGTATCATCCCCGATAGGGAAGTT-3' comprising a recognition site of SacII and the 5422nd to the 5442nd nucleotides of KHCV-LBC1; and Primer PNS4ESAL (SEQ ID NO: 30): 5'-AAAAAAGTC GACTATTACAACCCGAGCGCCTTCTGTTT-3' comprising a stop codon to terminate translation after the 5547th nucleotide of KHCV-LBC1, and a recognition site of SalI.

(1-2) Polymerase chain reaction

A test tube was provided with the primer PNS4ET2 2 μg and primer PNS4ESAL 2 μg. To the tube were added 50 ng of KHCV-LBC1 DNA(ATCC 75008), 10 μl of 10x polymerase buffer solution, 10 μl of 2 mM dNTP(2 mM dGTP, 2 mM dATP, 2 mM TTP, 2 mM dCTP), 2.5 unit of Taq polymerase; and distilled water was added thereto to adjust the total volume to be 100 μl.

To the reaction mixture was added 5 μl of mineral oil to prevent evaporation; and PCR was carried out by repeating 25 times the same thermal cycles as in Reference Example 6.

(1-3) Separation and purification of PCR product

The PCR product obtained in the above (1-2) was subjected to 5% polyacrylamide gel electrophoresis. As a result, it was confirmed that about 130 bp of DNA was amplified. The DNA was purified by the same polyacrylamide gel electrophoresis as above and named fragment NS4E.

<Step 2> Preparation of expression vector

2 μg of fragment NS4E obtained in the above (1-3) was completely digested with SacII and SalI in NEB buffer solution 3 referred to in Reference Example 1.

A ligation tube was provided with 100 ng of DNA fragment obtained above. To the tube were added 50 ng of fragment ptrpH-UB-T2/L obtained in <Step 2> of Example 1, 2 μl of 10x ligation buffer solution, 10 units of T4 DNA ligase; and distilled water was added to adjust the total volume to be 20 μl. The ligation was carried out at 16° C. for 12 hours.

*E. coli* W3110(ATCC 37339) was transformed with the ligation mixture to obtain recombinant *E. coli* cell containing plasmid ptrpH-UB-NS4E comprising fragment NS4E (FIG. 12).

<Step 3> Preparation of KHCV E1E2 protein (3-1) Preparation of primers

In order to amplify KHCV E1E2 gene which comprising the epitopes of HCV envelope protein and to clone it into an expression vector comprising ubiquitin gene under the control of trp promotor, the following primers were synthesized:

Primer PE2ET2 (SEQ ID NO: 22): 5'-TGAGACTCC GCGGTGGTACTCGGGGAGAGCGTTGTGAC-3' comprising a recognition site of SacII and the 2281st to the 2298th nucleotides of KHCV-LBC1;

Primer PE2EGE1G (SEQ ID NO: 31): 5'-TTCCTTCTT CTGGCGGACGCGGTTTCCCAGCTGTTCACCTTC-3' comprising the region from the 2509th to the 2529th nucleotides of KHCV-LBC1, which is the 3'-end region of E2E DNA, and the region from the 1201st to the 1221st nucleotides of KHCV-LBC1 which is the 5'-end region of E1G gene; and Primer PE2AXHO (SEQ ID NO: 23): 5'-AAAAAACTC GAGTTACCACCCCTGCGCGAATGTATC-3' comprising a stop codon to terminate translation after the 1749th nucleotide of KHCV-LBC1, and a recognition site of XhoI.

(3-2) Polymerase chain reaction

A test tube was provided with the primer PE2EGE1G 2 μg and primer PE2AXHO 2 μg. To the tube were added 50 ng of KHCV-LBC1 DNA(ATCC 75008) as a template, 10 μl of 10x polymerase buffer solution, 10 μl of 2 mM dNTP(2 mM dGTP, 2 mM dATP, 2 mM TTP, 2 mM dCTP), 2.5 unit of Taq polymerase; and distilled water was added thereto to adjust the total volume to be 100 μl.

To the reaction mixture was added 50 μl of mineral oil to prevent evaporation; and PCR was carried out by repeating 25 times the same thermal cycles as in Reference Example 6.

(3-3) Separation and purification of PCR product

The PCR product obtained in the above (3-2) was subjected to 5% polyacrylamide gel electrophoresis. As a result, it was confirmed that about 550 bp of DNA was amplified. The DNA was purified by the same polyacrylamide gel electrophoresis as above-and named fragment GE1GE2A.

(3-4) Second Polymerase chain reaction

A test tube was provided with the primer PE2ET2 2 μg and primer PE2AXHO 2 μg. To the tube were added 50 ng of plasmid pYLBC-A/G-UBE2C(ATCC 74117, see Korean Patent Laid-open Publication No. 93-683) and fragment GE1GE2A obtained in the above (3-3) as templates, 10 μl of 10x polymerase buffer solution, 10 μl of 2 mM dNTP(2 mM dGTP, 2 mM dATP, 2 mM TTP, 2 mM dCTP), 2.5 unit of Taq polymerase; and distilled water was added thereto to adjust the total volume to be 100 μl.

To the reaction mixture was added 50 μl of mineral oil to prevent evaporation; and PCR was carried out by repeating 25 times the same thermal cycles as in Reference Example 6.

(3-5) Separation and purification of PCR product

The PCR product obtained in the above (3-4) was subjected to 5% polyacrylamide gel electrophoresis. As a result, it was confirmed that about 800 bp of DNA was amplified. The DNA was purified by the same polyacrylamide gel electrophoresis as above and named fragment E1E2.

(3-6) Preparation of expression vector

2 μg of DNA fragment obtained in (3-5) was completely digested with SacII and XhoI in NEB buffer solution 3 in accordance with Reference Example 1.

A tube was provided with 100 ng of DNA fragment obtained above. To the tube were added 50 ng of fragment ptrpH-UB-T2/L obtained in <Step 2> of Example 1, 2 μl of 10 x ligation buffer solution, 10 units of T4 DNA ligase; and distilled water was added to adjust the total volume to be 20 μl. The ligation was carried out at 16° C. for 12 hours.

Figure 13:
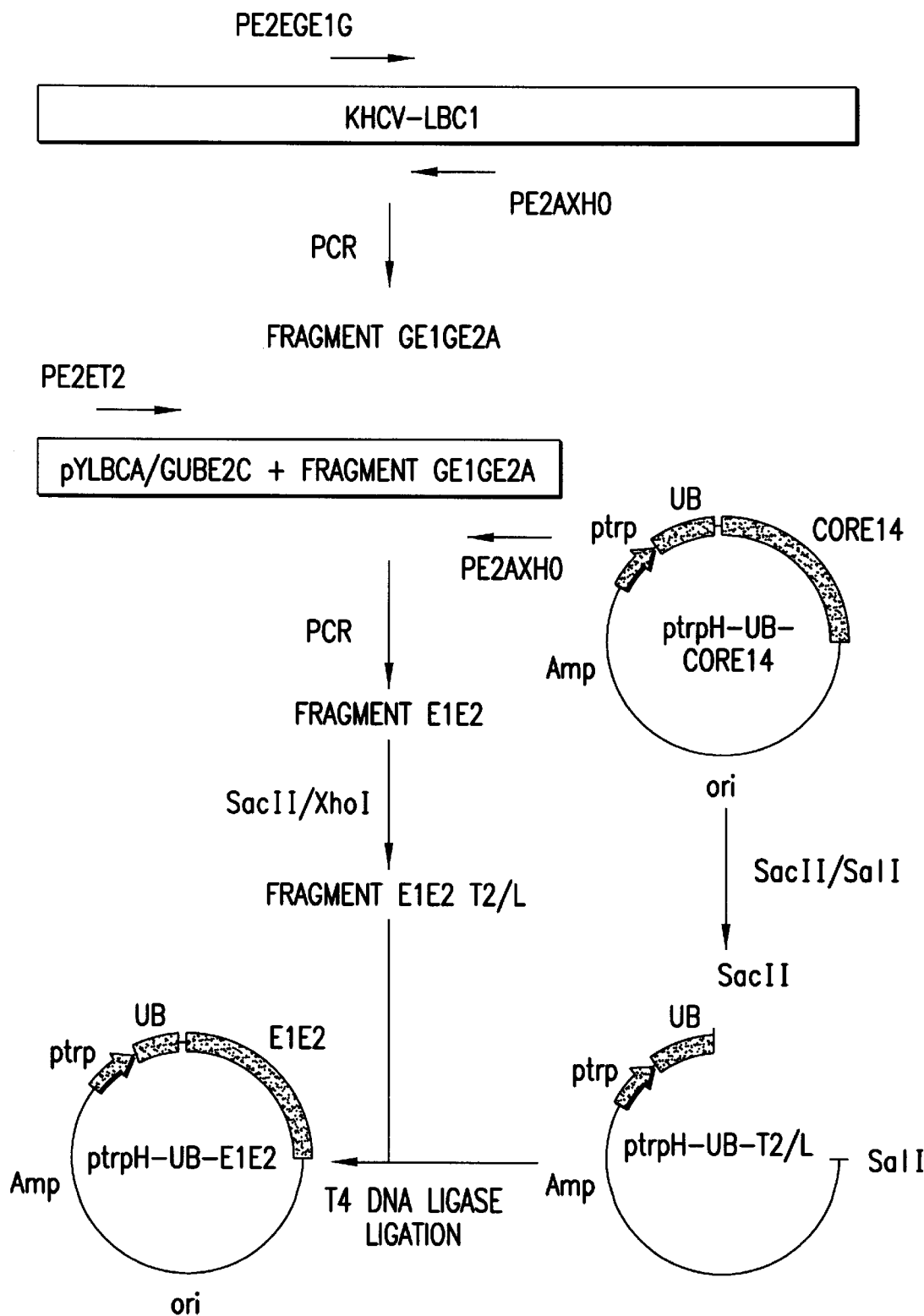
FIG. 13 shows a schematic diagram for preparing an expression vector constructed for the purpose of expressing a recombinant DNA encoding UBE1E2 protein comprising ubiquitin and the fusion protein E1E2 containing epitopes of envelope protein, E1G, E2A and E2E.

E. coli W3110(ATCC 37339) was transformed with the ligation mixture to obtain recombinant E. coli cell containing plasmid ptrpH-UB-E1E2 comprising the fragment E1E2 (FIG. 13).

(3-7) Expression of E1E2 DNA

E. coli W3110(ATCC 37339) cells transformed with the plasmid ptrpH-UB-E1E2 prepared in the above (3-6) were cultured in the same manner as in <Step 3> of Example 1; and then centrifuged to collect the E. coli cell precipitates.

Figure 14A:
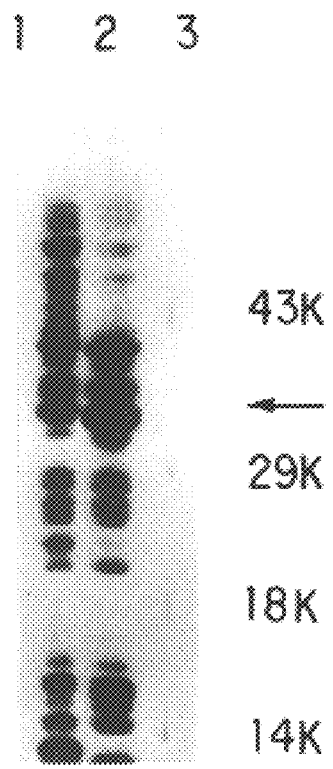
FIG. 14A shows the result of SDS polyacrylamide gel electrophoresis(SDS-PAGE) after the expression of recombinant UBE1E2 protein in *E. coli* cells.
Figure 14B:
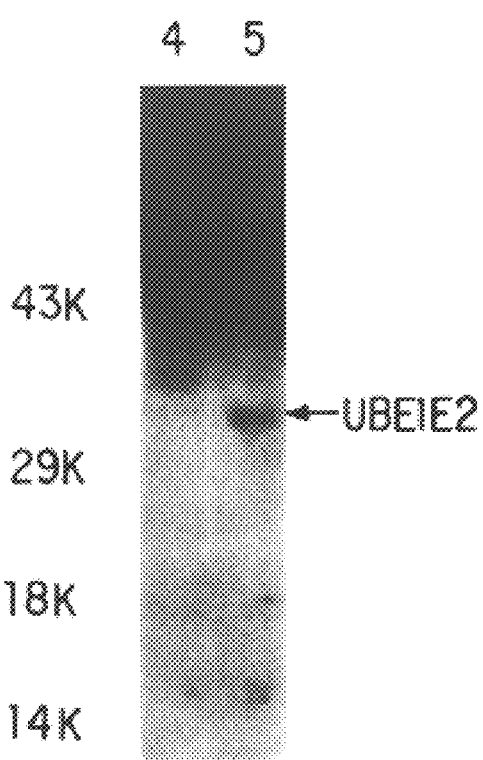
FIG. 14B shows the result of western blotting analysis with the gel of FIG. 14A by using a serum taken from a hepatitis C patient.
Figure 15:
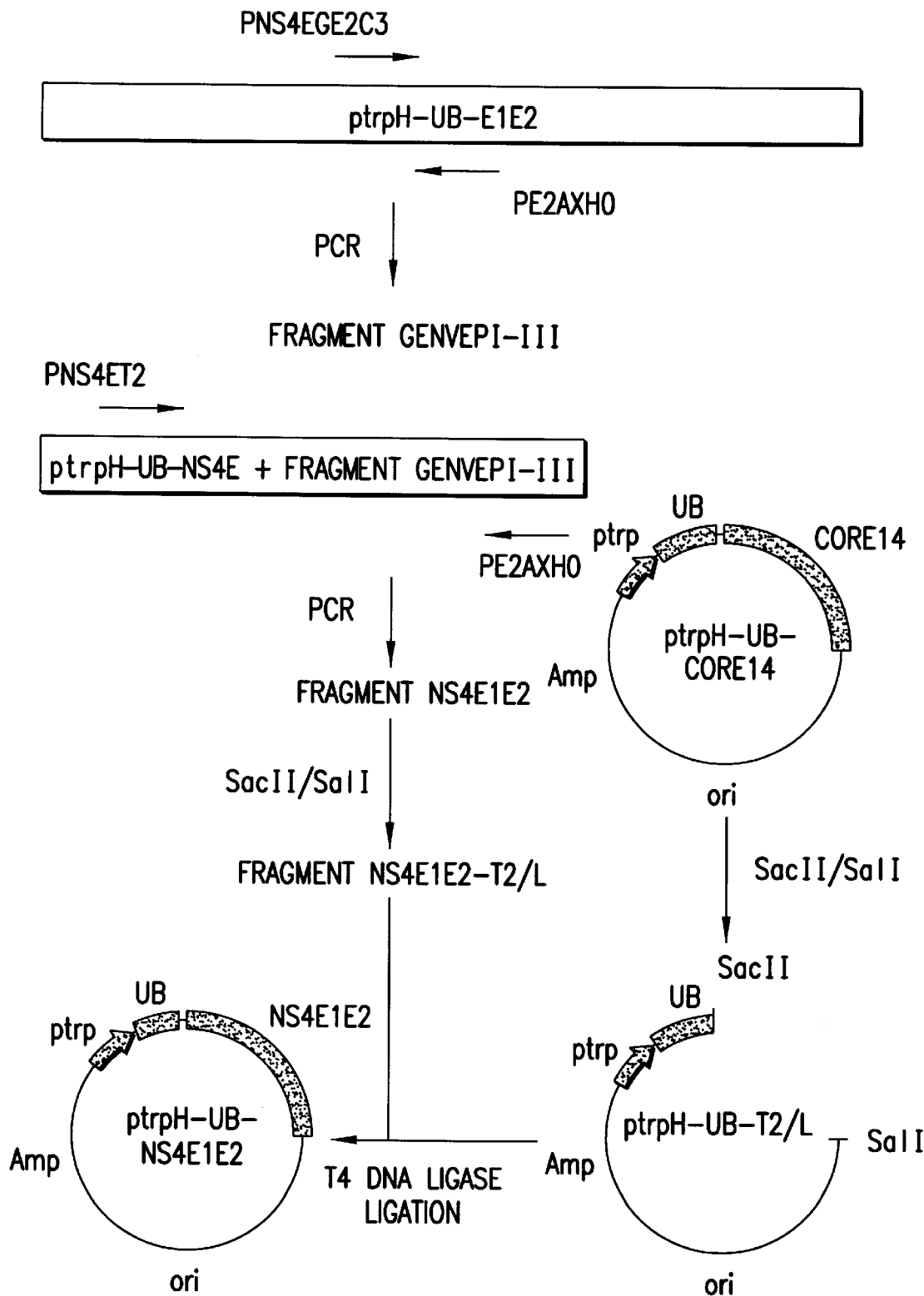
FIG. 15 shows a schematic diagram for preparing an expression vector constructed for the purpose of expressing a recombinant DNA encoding UBNS4E1E2 protein comprising ubiquitin, NS4E protein and E1E2 protein.

(3-8) Confirmation of expressed UBE1E2 protein and reactivity thereof with a serum taken from a hepatitis C patient Expression of UBE1E2 protein and their reactivity with a serum taken from a hepatitis C patient were confirmed by employing the cell precipitates of (3-7) in the same manner as in <Step 4> of Example 1; and the result is shown in FIG. 14, wherein A is the result of SDS-PAGE and B is the result of Western blotting.

In FIGS. 14A and B, lanes 1 and 4 show the products of E. coli not having plasmid ptrpH-UB-E1E2; lanes 2 and 5 show the products of E. coli transformed with ptrpH-UB-E1E2; and lane 3 shows the standard molecular size markers, i.e., 43, 29, 18 and 14 kilodaltons from the top of the gel.

<Step 4> Preparation of KHCV NS4E1E2 protein
<Step 4-A> Amplification of NS4E1E2.gene
(4-A-1) Preparation of primers In order to amplify a gene which encodes the epitopes of HCV envelope protein and a part of KHCV NS4E DNA and to clone it into an expression vector comprising ubiquitin gene under the control of trp promotor, the following primers were synthesized.

Primer PNS4ET2 (SEQ ID NO: 29): 5'-TGAGACTCCG CGGTGGTATCATCCCCGATAGGGAAGTT-3' comprising a recognition site of SacII and the 5422nd to the 5442nd nucleotides of KHCV-LBC1;

Primer PNS4EGE2C3 (SEQ ID NO: 32): 5'-CAGAAGG CGCTCGGGTTGCCAGGAGGAGGAGGTGGTA CTCGGGGAGAGCGTTGT-3'comprising the region from the 5530th to the 5547th nucleotides of KHCV-LBC1, which is the 3'-end region of NS4E DNA, one proline codon, six-glycine codons and the region from the 2281st to the 2298th nucleotides of KHCV-LBC1, which is the 5'-end region of E2E gene, in that order; and Primer PE2AXHO (SEQ ID NO: 23): 5'-AAAAAACT CGAGTTACCACCCCTGCGCGAATGTATC-3' comprising a stop codon to terminate translation after the 1749th nucleotide of KHCV-LBC1, and a recognition site of XhoI.

(4-A-2) Polymerase chain reaction

A test tube was provided with 2 $\mu$g of primer PNS4EGE2C3 and 2 $\mu$g of primer PE2AXHO. To the tube were added 50 ng of ptrpH-UB-E1E2((3-6) of <Step 3>) as a template, 10 $\mu$l of 10x polymerase buffer solution, 10 $\mu$l of 2 mM dNTP(2 mM dGTP, 2 mM dATP, 2 mM TTP, 2 mM dCTP), 2.5 unit of Taq polymerase; and distilled water was added thereto to adjust the total volume to be 100 $\mu$l.

To the reaction mixture was added 50 $\mu$l of mineral oil to prevent evaporation; and PCR was carried out by repeating 25 times the same thermal cycles as in Reference Example 6.

(4-A-3) Separation and purification of PCR product

The PCR product obtained in the above (4-A-2) was subjected to 5% polyacrylamide gel electrophoresis. As a result, it was confirmed that about 800 bp of DNA was amplified. The DNA was purified by the same polyacrylamide gel electrophoresis as above and named fragment GENVEPI-III.

(4-A-4) Second Polymerase chain reaction

A test tube was provided with 2 $\mu$g of primer PNS4ET2 and 2 $\mu$g of primer PE2AXHO. To the tube were added 50 ng of plasmid ptrpH-UB-NS4E obtained in the above <Step 1> as a template, 50 ng of fragment GENVEPI-III obtained in the above (4-A-2), 10 $\mu$l of 10x polymerase buffer solution, 10 $\mu$l of 2 mM dNTP(2 mM dGTP, 2 mM dATP, 2 mM TTP, 2 mM dCTP), 2.5 unit of Taq polymerase; and distilled water was added thereto to adjust the total volume to be 100 $\mu$l.

To the reaction mixture was added 50 $\mu$l of mineral oil to prevent evaporation; and PCR was carried out by repeating 25 times the same thermal cycles as in Reference Example 6.

(4-A-5) Separation and purification of PCR product

The PCR product obtained in the above (4-A-4) was subjected to 5% polyacrylamide gel electrophoresis. As a result, it was confirmed that about 920 bp of DNA was amplified. The DNA was purified by the same polyacrylamide gel electrophoresis as above and named fragment NS4E1E2.

<Step 4-B> Preparation of expression vector

2 $\mu$g of the DNA fragment obtained in (4-A-5) of <Step 4-A> was completely digested with SacII and XhoI in NEB buffer solution 3 referred to in Reference Example 1.

A tube was provided with 100 ng of DNA fragment obtained above. To the tube were added 50 ng of the fragment ptrpH-UB-T2/L obtained in <Step 2> of Example 1, 2 $\mu$l of 10x ligation buffer solution, 10 units of T4 DNA ligase; and distilled water was added to adjust the total volume to be 20 $\mu$l. The ligation was carried out at 16° C. for 12 hours.

*E. coli* W3110(ATCC 37339) was transformed with the ligation mixture to obtain recombinant *E. coli* cell containing plasmid ptrpH-UB-NS4E1E2 comprising the fragment NS4E1E2(FIG. 15).

<Step 4-C> Expression of the fragment NS4E1E2 DNA

*E. coli* W3110(ATCC 37339) transformant harboring plasmid ptrpH-UB-E1E2 prepared in the above <Step 4-B> were cultured in the same manner as in <Step 3> of Example 1; and then centrifuged to collect the *E. coli* cell precipitates.

<Step 4-D> Confirmation of expressed UBNS4E1E2 protein and reactivity thereof with a serum taken from a hepatitis C patient Production of UBNS4E1E2 protein in *E. coli* and their reactivity with a serum taken from a hepatitis C patient were confirmed by employing the cell precipitates of <Step 4-C> in the same manner as in <Step 4> of Example 1; and the result is shown in FIG. 16, wherein A is the result of SDS-PAGE and B is the result of western blotting.

In FIGS. 16A and B, lanes 1 and 4 show the products of *E. coli* not having plasmid ptrpH-UB-NS4E1E2; lanes 2 and 5 show the products of *E. coli* transformed with ptrpH-UB- NS4E1E2; and lane 3 shows the standard molecular size markers, i.e., 92, 70, 43, 29 and 18 kilodaltons from the top of the gel.

<Step 4-E> Purification of UBNS4E1E2 protein (4-E-1) Cell disruption and removal of soluble proteins 2 g of E. coli cell precipitate obtained in <Step 4-C> was treated as in <Step 4> (4-1) of Example 3 to disrupt the cell and obtain insoluble precipitate therefrom.

(4-E-2) Washing of insoluble precipitate

The precipitate obtained in (4-E-1) was treated as in <Step 4> (4-2) of Example 3 to remove dissolved proteins and obtain insoluble precipitate.

(4-E-3) Washing with 4M urea

The insoluble precipitate of (4-E-2) was suspended in 30 ml of buffer 2 containing 4M urea. The suspension was stirred at room temperature for 2 hours and centrifuged at 15,000 rpm with a centrifuge(Beckman J2-21, Rotor JA 20) to remove dissolved proteins and obtain insoluble precipitate.

(4-E-4) Washing with 6M guanidine chloride

The insoluble precipitate of (4-E-3) was suspended in 30 ml of buffer 2 containing 6M guanidine chloride. The suspension was stirred at room temperature for 2 hours and centrifuged at 15,000 rpm with a centrifuge(Beckman J2-21, Rotor JA 20) to remove dissolved proteins and obtain insoluble precipitate.

(4-E-5) Dissolution of precipitate with 1% SDS

The insoluble precipitate of (4-E-4) was suspended in 10 ml of PBS(10 mM phosphate, pH 7.0, 150 mM NaCl) containing 1% SDS. The suspension was stirred at room temperature for 12 hours and centrifuged at 15,000 rpm with a centrifuge(Beckman J2-21, Rotor JA 20) to remove insoluble precipitate and obtain supernatant.

(4-E-6) S-300 gel filtration chromatography 10 ml of the supernatant obtained in (4-E-5) were concentrated to a volume of 4 ml with YM10 ultrafiltration membrane(Amicon, U.S.A.) and then, centrifuged at 15,000 rpm for 25 minutes with a centrifuge(Beckman J2-21, Rotor JA 20) to remove insoluble precipitate and obtain supernatant. The supernatant was subjected to gel filtration chromatography with S-300 resin column(Pharmacia LKB, 2.5 cm×90 cm) equilibrated with PBS containing 0.1% SDS at a flow rate of 40 ml/hour. The eluted protein was collected by 2 ml fractions and subjected to 15% SDS-PAGE to collect the fractions comprising UBNS4E1E2 protein having a purity of at least 90%; and the antigenic specificity of the purified protein was confirmed by employing a western blotting analysis.

Example 5

Preparation of KHCV NS5-1.2 Protein

<Step 1> Amplification of NS5-1.2 DNA (1-1) Preparation of primers

In order to amplify KHCV NS5-1.2 DNA(which consists of the region from the 6649th to the 7824th nucleotides of KHCV-LBC1) and to clone it into an E. coli expression vector comprising ubiquitin gene under the control of trp promotor, the following primers were synthesized.

Primer PNS5T2 (SEQ ID NO: 33): 5'-TGAGACTCC GCGGTGGTACGGGCATGACCACTGACAAC-3' comprising a recognition site of SacII and the 6649th to the 6669th nucleotides of KHCV-LBC1; and Primer PNS5-1.2SAL (SEQ ID NO: 34): 5'-AAAAAGTC GACTATTACGCCTTCCCCTTCATCTCCTT-3' comprising a stop codon to terminate translation after the 7824th nucleotide of KHCV-LBC1, and a recognition site of SalI.

(1-2) Polymerase chain reaction

A test tube was provided with 2 $\mu$g of primer PNS5T2 and 2 $\mu$g of primer PNS5-1.2SAL. To the tube were added 50 ng of KHCV-LBC1 DNA(ATCC 75008) as a template, 10 $\mu$l of 10x polymerase buffer solution, 10 $\mu$l of 2 mM dNTP(2 mM dGTP, 2 mM dATP, 2 mM TTP, 2 mM dCTP), 2.5 unit of Taq polymerase; and distilled water was added thereto to adjust the total volume to be 100$\mu$l.

To the reaction mixture was added 50 $\mu$l of mineral oil to prevent evaporation; and PCR was carried out by repeating 25 times the same thermal cycles as in Reference Example 6.

(1-3) Separation and purification of PCR product

The PCR product obtained in the above (1-2) was subjected to 5% polyacrylamide gel electrophoresis. As a result, it was confirmed that about 1.2 Kb of DNA was amplified. The DNA was purified by the same polyacrylamide gel electrophoresis as above and named fragment NS5-1.2.

<Step 2> Preparation of expression vector

2 $\mu$g of DNA fragment obtained in (1-3) of <Step 1> was completely digested with SacII and SalI in NEB buffer solution 3 referred to in Reference Example 1.

A tube was provided with 100 ng of DNA fragment obtained above. To the tube were added 50 ng of fragment ptrpH-UB-T2/L obtained in <Step 2> of Example 1, 2 $\mu$l of 10x ligation buffer solution, 10 units of T4 DNA ligase; and distilled water was added to adjust the total volume to be 20 $\mu$l. The ligation was carried out at 16° C. for 12 hours.

*E. coli* W3110(ATCC 37339) was transformed with the ligation mixture to obtain recombinant *E. coli* cell containing plasmid ptrpH-UB-NS5-1.2 comprising fragment NS5-1.2(FIG. 17).

<Step 3> Expression of the fragment NS5-1.2 DNA

*E. coli* W3110(ATCC 37339) cells transformed with the plasmid ptrpH-UB-NS5-1.2 prepared in the above <Step 2> were cultured in the same manner as in <Step 3> of Example 1; and then centrifuged to collect the *E. coli* cell precipitates.

<Step 4> Confirmation of expressed KHCV UBNS5-1.2 protein and reactivity thereof with a serum taken from a hepatitis C patient Production of UBNS5-1.2 protein in *E. coli* and their reactivity with a serum taken from a hepatitis C patient were confirmed by employing the cell precipitates of <Step 3> in the same manner as in <Step 4> of Example 1; and the result is shown in FIG. 18, wherein A is the result of SDS-PAGE and B is the result of western blotting.

In FIGS. 18A and B, lane 1 shows the products of *E. coli* not having plasmid ptrpH-UB-NS5-1.2; and lanes 2 and 3 show the products of *E. coli* transformed with ptrpH-UB-NS5-1.2.

<Step 5> Comparison of reactivity of KHCV UBNS5-1.2 protein with a serum taken from a hepatitis C patient to that of KHCV403 protein Reactivity of UBNS5-1.2 protein with a serum taken from a hepatitis C patient was confirmed by employing the cell precipitates obtained in the above <Step 3> in the same manner as in <Step 4> of Example 1; and the result was compared to that of KHCV 403 protein which was confirmed by employing the yeast cell precipitate wherein KHCV 403 protein was produced according to Korean Laid-open Publication No. 93-12107 in the same manner as above. The results are shown in FIG. 19, wherein A is the result of SDS-PAGE and B is the result of Western blotting.

In FIGS. 19A and B, lane 1 shows the products of Saccharomyces cerevisiae DCO4-UB-KHCV 403(ATCC 74709); and lanes 2 shows the products of *E . coli* transformed with ptrpH-UB-NS5-1.2. From the result, it is confirmed that UBNS5-1.2 protein has much stronger reactivity with the serum taken from a hepatitis C patients than KHCV 403 protein.

<Step 6> Purification of UBNS5-1.2 protein (6-1) Cell disruption and removal of soluble proteins 3 g of E. coli cell precipitate obtained in <Step 3> was treated as in <Step 4> (4-1) of Example 3 to disrupt the cell and obtain insoluble precipitate therefrom.

(6-2) Washing of insoluble precipitate

The precipitate obtained in (6-1) was treated as in <Step 4> (4-2) of Example 3 to remove dissolved proteins and obtain insoluble precipitate.

(6-3) Dissolution of insoluble precipitate

The insoluble precipitate of (6-2) was suspended in 100 ml of buffer 3(50 mM Tris, pH 9.0, 1 mM EDTA, 10 mM β-mercapto-ethanol) containing 8M urea. The suspension was stirred at room temperature for 1 hours and centrifuged to remove insoluble precipitate and obtain the supernatant.

(6-4) DEAE-Sepharose ion exchange chromatography

The supernatant obtained in (6-3) was passed through DEAE-Sepharose column(Pharmacia, 2.5 cm×3 cm) equilibrated with the above buffer 3 at a flow rate of 2 ml/min.; and same buffer was added to elute free proteins remains in column. Then, 300 ml of buffer 3 having a concentration gradient of 0 to 0.3M NaCl was added at a flow rate of 8ml/min. to elute the bound proteins and collect the eluate by 4 ml fractions. The protein fractions were subjected to 15% SDS-PAGE to collect the fractions comprising UBNS5-1.2 protein.

(6-5) S-300 gel filtration chromatography

The protein fractions collected in (6-4) was concentrated to a volume of 3 ml with YM10 ultrafiltration membrane (Amicon, U.S.A.), and then, passed over S-300 resin column (Pharmacia, 1.2 cm×120 cm) equilibrated with buffer 3 containing 8M urea at a flow rate of 10 ml/hour. The eluted protein was collected by 0.5 ml fractions and subjected to 15% SDS-PAGE to collect the fractions comprising highly pure UBNS5-1.2 protein.

(6-6) FPLC-phenyl-superose chromatography

The protein fractions collected in (6-5) were passed over YM10 ultrafiltration membrane (Amicon, U.S.A.) to concentrate to a volume of 4 ml. The concentrate was dialyzed against PBS(10 mM phosphate, pH 7.0, 15 mM NaCl) using a dialysis membrane(Spectrum Medical Industries, Inc., M. W. cut off 6,000–8,000) to remove urea. To the solution was added sodium chloride to a final concentration of 1.5M. The resultant was passed over FPLC-phenyl-superose column (Pharmacia, HR 5/5, 0.5 cm×5 cm) equilibrated with the same buffer at a flow rate of 0.7 ml/min.; and the same buffer was added to elute free proteins remained in column. Then, PBS containing a linear concentration gradient of 1.5M to 0 M sodium chloride was added to elute the bound proteins and collect the eluate by 0.7 ml fractions. The protein fractions were subjected to 15% SDS-PAGE to collect the fractions comprising UBNS5-1.2 protein having a purity of at least 95%; and the antigenic specificity of the purified protein was confirmed by employing a western blotting analysis.

Example 6

Detection of Anti-HCV Antibodies with Individual KHCV Proteins and Recombinant Proteins of the Present Invention by Employing ELISA(Enzyme-Linked Immunosorbent Assay) Method Each of KHCV CORE 14, KHCV 403 and KHCV NS5-1.2 protein was diluted with 50 mM sodium borate buffer(pH 9.0) to a concentration of 0.3 μg/ml. KHCV E2C and KHCV E1 protein were also diluted with the same buffer to a concentration of 0.2 μg/ml and 0.1 μg/ml, respectively. The diluted protein solutions were added to the wells of a microtiter plate(Dynatech, Immulon type 1 microtiter plate) in an amount of 200 μl/well and incubated at 37° C. for 2 hours.

The plate was washed once with PBS containing 0.05% (v/v) Tween-20(pH 7.4, hereinafter referred to as "washing solution"). PBS containing 0.1%(w/v) gelatin was added to the wells in an amount of 250 μl/well; and the plate was incubated at 37° C. for 1 hours to block the remaining protein adsorption sites so as to prevent any non-specific reactions which may occur later. The wells were washed twice with said washing solution and 190 μl of PBS containing 0.25% gelatin, 1.0%(v/v), Triton X-100, 1 mM EDTA and 0.02% Thimerosal was added to every well. Then, 10 μl of serum samples taken from a HCV patient and a normal donor was added thereto and mixed gently for several seconds.

The wells which were reacted at 37° C. for 1 hour were washed five times with the washing solution; and a solution comprising anti-human IgG antibody labelled with horse-radish peroxidase(HRP)(Bio-Rad Company, Richmond, Calif. 94804, U.S.A, 0.1 mg protein/ml) which was diluted to a concentration of 1 μg/ml with PBS containing 10% fetal bovine serum(v/v), 1% Ficoll(Sigma, v/v), 0.05% Tween-20 and 0.02% Thimerosal was added to the wells in an amount of 200 μl/well.

The resultant was incubated at 37° .C for 1 hour and washed 5 times with said washing solution. Thereafter, 200 μl of substrate solution prepared by dissolving O-phenylene diamine dihydrochloric acid tablet(OPD tablet, Sigma) with 50 mM citrate buffer to a concentration of 10 mg/ml and adjusting to pH 5.5 by adding phosphate was added to each well and incubated at room temperature for 30 minutes in the dark. To the resultant was added 50 μl of 4N sulfuric acid per each well to stop the color development; and O.D. of each well was determined at the wavelength of 492 nm with Multiscan titertek(Flow Lab).

In addition, the same procedures as above were repeated by employing a mixed antigen solution comprising 250 ng of KHCV CORE 518 protein, 125 ng of KHCV NS4E1E2 protein and 125 ng of KHCV NS5-1.2 protein per 1 ml of 50 mM sodium borate buffer(pH 9.0).

The results of the above procedures for detecting anti-KHCV antibodies by employing individual KHCV antigens and mixed antigens are shown in Table II below.

TABLE II

Detection of anti-HCV antibody with individual KHCV antigen and mixed antigens of the present invention

| antigen Sample No. | KHCV CORE14 | KHCV 897 | KHCV 403 | KHCV NS5-1.2 | KHCV E1 | KHCV E2 | Mixed antigens |
|---|---|---|---|---|---|---|---|
| 1 | 7.98 | 7.35 | 1.28 | 5.83 | 6.08 | 0.50 | 10.12 |
| 2 | 7.77 | 7.29 | 6.43 | 5.81 | 4.19 | 0.84 | 10.0 |
| 3 | 3.31 | 6.98 | 6.77 | 5.06 | 0.68 | 0.18 | 5.70 |
| 4 | 7.89 | 7.06 | 0.86 | 0.23 | 5.32 | 0.83 | 9.08 |

TABLE II-continued

Detection of anti-HCV antibody with individual KHCV antigen and mixed antigens of the present invention

| antigen Sample No. | KHCV CORE14 | KHCV 897 | KHCV 403 | KHCV NS5-1.2 | KHCV E1 | KHCV E2 | Mixed antigens |
|---|---|---|---|---|---|---|---|
| 5 | 7.71 | 7.21 | 0.96 | 2.35 | 4.48 | 2.19 | 8.41 |
| Positive control | 7.53 | 7.35 | 7.44 | 5.87 | 5.95 | 8.89 | 8.83 |
| Negative control | 0.25 | 0.26 | 0.25 | 0.41 | 0.43 | 0.11 | 0.17 |

Note)
1. Each numerical value represents the absorbance/cutoff value
2. Positive control: HIV (−), HBV (−), HCV (+)
Negative control: HIV (−), HBV (−), HCV (−)
3. The serum samples including positive and negative controls were provided by Korean Red Cross Blood Center In the above test, cutoff value was determined as follows:

509 HCV-negative and 76 HCV-positive serum samples confirmed with RIBA II diagnostic kit(Ortho Diagnostic Systems, U.S.A.) by employing immunoblotting assay method were tested according to the above diagnostic process to obtain the result shown in Table III.

TABLE III

|  | Number of samples | Average of $OD_{490}$ | Standard deviation |
|---|---|---|---|
| negative sample | 509 | 0.098 | 0.095 |
| positive sample | 76 | 1.791 | 0.809 |

Then, cutoff value was calculated by employing the following general equation for adjusting cutoff value:

Cutoff value=average of $OD_{490}$ of negative samples +3× standard deviation of $OD_{490}$ of negative samples Accordingly, a cutoff value of 0.4 was obtained by reference to the calculated cutoff value of 0.383 and the distribution of $OD_{490}$ of negative samples.

As can be seen from the above Table II, individual antigen, as well as the mixed antigen may be used as a diagnostic agent for detecting anti-HCV antibody; however the mixed antigen shows more sensitive and district results between negative and positive samples.

Example 7

Detection of Anti-KHCV Antibodies by Employing Individual Recombinant Protein Comprising KHCV Epitopes and Mixed KHCV Antigens Each of KHCV E1E2 and KHCV NS4E1E2 proteins was diluted with 50 mM sodium borate buffer(pH 9.0) to a concentration of 0.2 μg/ml; and an antigen solution comprising 250 ng of KHCV CORE 518 protein, 125 ng of KHCV NS4E1E2 protein and 125 ng of NS5-1.2 protein per 1 ml of 50 mM sodium borate buffer(pH 9.0) was prepared. The diluted protein solutions were added to the wells of a microtiter plate(Dynatech, Immulon type 1 microtiter plate) in an amount of 200 μl/well and the same procedures as in the Example 6 were repeated to obtain the result shown in Table IV below.

TABLE IV

Detection of anti-HCV antibody with mixed antigens

| antigen Sample No. | KHCV E1E2 | KHCV NS4E1E2 | mixed antigens |
|---|---|---|---|
| 1 | 0.222 | 0.233 | 0.180 |
| 2 | 7.834 | 8.10 | 8.301 |
| 3 | 4.554 | 7.067 | 8.14 |
| 4 | 0.255 | 0.233 | 0.190 |
| 5 | 0.573 | 7.700 | 7.470 |
| 6 | 0.255 | 0.300 | 0.217 |
| 7 | 0.478 | 0.700 | 0.640 |
| 8 | 0.446 | 0.533 | 0.314 |
| 9 | 0.032 | 0.067 | 0.090 |
| 10 | 0.510 | 0;433 | 0.303 |
| 11 | 0.478 | 9.460 | 0.467 |
| 12 | 0.350 | 0.667 | 0.737 |
| 13 | 7.548 | 7.900 | 8.755 |
| 14 | 7.675 | 8.133 | 8.502 |
| 15 | 0.573 | 0.060 | 0.294 |
| 16 | 0.669 | 0.567 | 0.377 |
| 17 | 0.414 | 0.433 | 0.257 |
| 18 | 0.382 | 0.460 | 0.304 |
| Positive control | 7.197 | 7.510 | 8.065 |
| Negative control | 0.280 | 0.250 | 0.193 |

Note)
1. Each numerical value represents the absorbance/cutoff value
2. Positive control: HIV (−), HBV (−), HCV (+)
Negative control: HIV (−), HBV (−), HCV (−)

As can be seen from the above Table IV, KHCV NS4E1E2 protein was more effective than KHCV E1E2 protein in detecting anti-KHCV antibodies from the serum taken from a hepatitis C patients, and the mixed antigens exhibited higher effectiveness than KHCV NS4E1E2 protein itself owing to the additive effect of other antigens included in the mixture.

In addition, each of KHCV COREEPI, KHCV 518 and KHCV CORE518 protein was diluted with 50 mM sodium borate buffer(pH 9.0) to a concentration of 125 ng/ml; the antigen solution was added to the wells of a microtiter plate(Dynatech, Immulon type 1 microtiter plate) in an amount of 200 μl/well; and the same procedures as in the Example 6 were repeated by employing 136 sera taken from hepatitis C patients(which were obtained from Hyundai Central Hospital, Seoul, Korea). The result obtained in the above procedure is shown in Table V comparatively with the result obtained by PCR method.

TABLE V

| KHCV COREEPI | KHCV 518 | KHCV CORE518 | PCR |
|---|---|---|---|
| 119 (+) | 83 (+) | 123 (+) | 123 (+) |
| 13 (−) | 11 (−) | 12 (−) | 13 (−) |

As can be seen from the above Table V, the diagnostic results obtained by employing the KHCV COREEPI protein and KHCV 518 protein were less sensitive than the diagnostic result obtained by employing the KHCV CORE518 protein which comprises epitopes of the above two KHCV proteins.

Example 8

Comparison of Diagnostic Methods of Prior Art and the Present Invention

The same procedures as in the Example 6 were repeated by employing samples obtained periodically from human HCV seroconversional panels after blood transfusion (Serological Inc., 780 Park North Blud, Clarkston, Ga. 30021, USA) to detect anti-HCV antibodies therein; and the result is shown in Table VI below, comparatively with the results obtained by employing Ortho 1st generation and Abbott 1st generation HCV diagnostic Kits.

TABLE VI

Detection of anti-HCV antibodies in seroconversional samples

| Days after blood transfusion | ALT mU/ml | AST mU/ml | Ortho first generation | Abbott first generation | mixed antigens | Confirm test RIBAII |
|---|---|---|---|---|---|---|
| 1 | 11 | — | 0.29 | 0.263 | 0.49 | − |
| 11 | 24 | — | 0.33 | 0.253 | 0.44 | − |
| 15 | 36 | — | 0.26 | 0.267 | 0.45 | − |
| 18 | 36 | — | 0.27 | 0.255 | 0.50 | − |
| 22 | 40 | — | 0.28 | 0.251 | 0.52 | − |
| 25 | 24 | — | 0.18 | 0.220 | 0.45 | − |
| 29 | 32 | — | 0.16 | 0.265 | 0.44 | − |
| 32 | 27 | 27 | 0.20 | 0.259 | 0.45 | − |
| 36 | 32 | — | 0.23 | 0.270 | 0.50 | − |
| 39 | 78 | — | 0.14 | 0.275 | 0.47 | − |
| 43 | 180 | 121 | 0.23 | 0.303 | 0.40 | − |
| 74 | 401 | 352 | 0.80 | 0.495 | 5.32 | + |
| 114 | 72 | 70 | 6.21 | 4.356 | 6.73 | + |
| 127 | 42 | 37 | 6.21 | 4.356 | 7.71 | + |
| 141 | 27 | 24 | 6.21 | 4.356 | 9.24 | + |
| 155 | 68 | 69 | 6.21 | 4.356 | 9.11 | + |
| 175 | 78 | 97 | 6.21 | 4.356 | 7.99 | + |
| 238 | 41 | 39 | 6.21 | 4.356 | 10.15 | + |
| 270 | 119 | 102 | 6.21 | 4.356 | 8.77 | + |
| 297 | 49 | 35 | 6.21 | 4.356 | 8.56 | + |
| 365 | 157 | 128 | 6.21 | 4.356 | 9.72 | + |
| 399 | 46 | 19 | 6.21 | 4.356 | 9.45 | + |

Note)
1. Each numerical value represents the absorbance/cutoff value
2. The activities of alanine aminotransferase(ALT) and aspartate aminotransferase(AST) are normally 0–50 mU/ml.
3. Ortho 1st generation HCV diagnostic kit was commercially available from Ortho Diagnostic Systems, U.S.A.
4. Abbott 1st generation HCV diagnostic kit was commercially available from Abbott Lab., U.S.A.
5. RIBA II HCV Test System was commercially available from Ortho Diagnostic Systems, U.S.A.

The above result reveals that the diagnostic kit of the present invention can detect anti-HCV antibodies more earlier (about 5–6 weeks earlier) than the other 1st generation diagnostic kits, and similar to RIBA II kit even though the diagnostic method of the present invention employs ELISA method which is more convenient than the immunoblotting assay adopted by RIBA II kit.

Example 9

Accuracy of Diagnosis

To demonstrate the accuracy of the result of the present diagnosis, 18 serum samples which had been diagnosed as positive by using the diagnostic kit for hepatitis C manufactured and sold by Ortho Diagnostic Systems were diagnosed again with the diagnostic kit of the present invention according to the process of Example 7; and also with the Ortho 2nd generation immunoblotting kit for diagnosing hepatitis C(Ortho Diagnostic Systems, U.S.A., Product Code 933491), which is recommended as a confirmation assay(Van der poel, C. L. et al., Lancet 337, 317–319 (1991)), in accordance with the manufacturer's instruction. These results are summarized in Table VII, which show that the diagnostic kit of the present invention has a lower false positive than Ortho's diagnostic kit for hepatitis C.

TABLE VII

Comparison of diagnostic result according to the present invention to that using Ortho 2nd generation diagnostic kit.

| Sample No. | Antigens of Ortho second generation recombinant immunoblotting kit | | | | | | Mixed antigens of the present invention |
|---|---|---|---|---|---|---|---|
| | 5-1-1 | C100-3 | C33C | C22-3 | SOD | judgement | |
| 1 | +/− | +/− | − | − | − | − | 0.180 |
| 2 | +4 | +4 | +4 | +4 | − | + | 8.301 |
| 3 | +1 | +4 | +4 | +4 | − | + | 8.141 |
| 4 | − | − | − | − | − | − | 0.190 |
| 5 | +1 | +4 | +4 | +4 | − | + | 7.470 |
| 6 | − | − | − | − | − | − | 0.217 |
| 7 | − | − | − | − | − | − | 0.640 |
| 8 | − | − | − | − | − | − | 0.314 |
| 9 | − | − | − | − | − | − | 0.090 |
| 10 | − | − | − | − | − | − | 0.303 |
| 11 | − | − | − | − | − | − | 0.467 |
| 12 | − | − | − | − | − | − | 0.737 |
| 13 | +2 | +1 | +3 | +4 | − | + | 8.755 |
| 14 | +/− | +/− | +4 | +4 | − | + | 8.502 |
| 15 | − | − | − | − | − | − | 0.294 |
| 16 | − | − | − | − | − | − | 0.377 |
| 17 | − | − | − | − | − | − | 0.257 |
| 18 | − | +/− | − | − | − | − | 0.304 |

Note)
If a sample found to have more than 1 in at least two antigens except the SOD control antigen, then it was judged to be positive.

Example 10

Specificity of the Diagnostic Kit

To demonstrate the specificity and sensitivity of the present diagnostic agent, 94 serum samples which had been diagnosed as positive by using any of the diagnostic kit for hepatitis C selected from a group consisting of Lucky I(which is the diagnostic kit developed by Lucky Limited and disclosed in Korean Patent Publication No. 93-683), Abbott 2nd generation diagnostic kit(Abbott II) and UBI (UBI Co., U.S.) were diagnosed again with the diagnostic kit of the present invention according to the process of Example 7. The results are summarized in Table VIII below.

As can be seen from Table VIII, all of the diagnostic kits exhibited similar sensitivities, and the diagnostic kit of the present invention(Lucky II) has higher specificity than other diagnostic kits for hepatitis C.

TABLE VIII

| Confirm test (RIBA II) | | Abbott II | UBI | Lucky I | Lucky II |
|---|---|---|---|---|---|
| Positve | + | 49 | 50 | 48 | 49 |
| 51 | − | 2 | 1 | 3 | 2 |
| Indeterminate | + | 6 | 4 | 5 | 2 |
| 8 | − | 2 | 4 | 3 | 6 |
| Negative | + | 6 | 19 | 10 | 2 |
| 35 | − | 29 | 16 | 25 | 33 |

*Judgement of the test results as true positive, true negative, false positive or false negative were carried out according to the result of RIBA II confirm test.

In addition, 278 serum samples were selected at random from the serum samples diagnosed as negative by using any of the above four diagnostic kits;(Abbott II, UBI, Lucky I and Lucky II) and the average absorbance($OD_{492}$) of the selected samples were calculated. The same procedures were repeated to obtain the average absorbance of 94 serum samples diagnosed as positive by using any of the diagnostic kit selected from a group consisting of Lucky I, Abbott II and UBI.

The average absorbance of positive samples(AVG of P) and average absorbance of negative samples(AVG of N) were divided respectively by average cutoff value to obtain average signal/cutoff(S/C) values of positive samples and negative samples. The results are shown in Table IX, below. As can be seen from Table IX, Lucky II and UBI have the largest differencees between the S/C values of positive and negative samples, which represents that they give clearer signal than others. However, the high S/C value of UBI is not significant, because it depends on some extent on the low cutoff value and, consequently, high false-positive rate may be resulted.

TABLE IX

| | Abbott II | UBI | Lucky I | Lucky II |
|---|---|---|---|---|
| AVG of P | 1.805 | 1.366 | 1.344 | 2.053 |
| AVG of N | 0.096 | 0.021 | 0.058 | 0.037 |
| Cutoff | 0.52 | 0.25 | 0.44 | 0.42 |
| S/C of P | 3.471 | 5.464 | 3.055 | 4.888 |
| S/C of N | 0.185 | 0.084 | 0.132 | 0.088 |

While the invention has been described with respect to the above specific embodiments, it should be recognized that various modifications and changes which may be apparent to those skilled in the art to which the invention pertains may be made and also fall within the scope of the invention as defined by the claims that follow.

---

What is claimed is:

1. A diagnostic reagent for detecting an antibody that binds a hepatitis C viral antigen in a sample, which reagent comprises a recombinant protein containing the amino acid sequence of one or more proteins selected from the group consisting of: KHCV COREEPI having the sequence of SEQ ID NO: 42, KHCV 518 having the sequence of SEQ ID NO: 43, KHCV NS4E having the sequence of SEQ ID NO: 44, KHCV E1G having the sequence of SEQ ID NO: 45, KHCV E2A having the sequence of SEQ ID NO: 46, KHCV E2E having the sequence of SEQ ID NO: 47, and KHCV NS5-1.2 having the sequence of SEQ ID NO: 48.

2. A diagnostic method for detecting an antibody directed against a hepatitis C viral antigen in a blood sample, comprising the steps of:
   (a) adsorbing the protein contained in the diagnostic reagent of claim 1 onto a solid support;
   (b) adding the blood sample to the solid support to form a complex of the protein and the antibody; and
   (c) determining the amount of the complex.

3. The diagnostic reagent of claim 1, wherein the recombinant protein is a fusion protein and comprises the amino acid sequences of KHCV COREEPI and KHCV 518 in this order.

4. The diagnostic reagent of claim 1, wherein the recombinant protein is a fusion protein and comprises the amino acid sequences of KHCV E1G, KHCV E2A and KHCV E2E in this order.

5. The diagnostic reagent of claim 1, wherein the recombinant protein is a fusion protein and comprises the amino acid sequences of KHCV NS4E, KHCV E1G, KHCV E2A and KHCV E2E in this order.

6. The diagnostic reagent of claim 1, wherein the recombinant protein is a fusion protein and further comprises the amino acid sequence of ubiquitin.

7. The diagnostic reagent of claim which comprises KHCV CORE-518 obtained by joining the sequences of SEQ ID NO: 42 and SEQ ID NO:43 in this order; KHCV NS4E1E2 obtained by joining the sequences of SEQ ID NO: 44, SEQ ID NO: 45, SEQ ID NO: 46 and SEQ ID NO: 47 in this order; and KHCV NS5 1.2 having the sequence of SEQ ID NO: 48.

* * * * *